United States Patent
Lee et al.

(10) Patent No.: US 9,284,555 B2
(45) Date of Patent: Mar. 15, 2016

(54) APTAZYME CAPABLE OF SELECTIVE SILENCING OF TARGET MIRNA BY RELEASING AN ANTISENSE SEQUENCE IN HEPATITIS C VIRUS-INFECTED CELLS AND USE THEREOF

(75) Inventors: Seong-Wook Lee, Seoul (KR); Chang-Ho Lee, Seoul (KR)

(73) Assignee: Industry-Academic Cooperation Foundation Dankook University (KR)

( * ) Notice: Subject to any disclaimer, the term of this patent is extended or adjusted under 35 U.S.C. 154(b) by 0 days.

(21) Appl. No.: 13/823,845

(22) PCT Filed: Sep. 16, 2011

(86) PCT No.: PCT/KR2011/006856
§ 371 (c)(1),
(2), (4) Date: Mar. 15, 2013

(87) PCT Pub. No.: WO2012/036507
PCT Pub. Date: Mar. 22, 2012

(65) Prior Publication Data
US 2013/0245094 A1    Sep. 19, 2013

(30) Foreign Application Priority Data
Sep. 16, 2010   (KR) .......................... 10-2010-0091145

(51) Int. Cl.
| | |
|---|---|
| *C12N 15/11* | (2006.01) |
| *C12Q 1/68* | (2006.01) |
| *C12N 15/113* | (2010.01) |
| *C12N 15/10* | (2006.01) |

(52) U.S. Cl.
CPC ........ *C12N 15/1131* (2013.01); *C12N 15/1068* (2013.01); *C12N 2310/128* (2013.01); *C12N 2310/16* (2013.01); *C12N 2310/3519* (2013.01); *C12N 2320/50* (2013.01)

(58) Field of Classification Search
CPC ................... C12Q 2521/337; C12Q 2521/161; C12Q 2521/205; C12Q 1/706; C12N 15/113; C12N 2310/12; C12N 2310/141
See application file for complete search history.

(56) References Cited

U.S. PATENT DOCUMENTS

| | | |
|---|---|---|
| 2003/0008295 A1 | 1/2003 | Usman et al. |
| 2004/0023292 A1 | 2/2004 | McSwiggen et al. |

OTHER PUBLICATIONS

Seong-Wook Lee et al., The Korean J. of Microbiology, vol. 43, No. 3, pp. 159-165 (2007).
Kumar, D. et al., J. Am. Chem. Soc. Communications, vol. 131, pp. 13906-13907 (2009).
Famulok, M. et al., Chemical Reviews, vol. 107, No. 9, pp. 3715-3743 (2007).
Bartenschlager, R., et al. Adv. Virus Res. vol. 63, pp. 71-180 (2004).
Chekulaeva, M., et al., Curr. Opin. Cell Biol. vol. 21, pp. 452-460 (2009).
Chang, J. et al., RNA Biol. vol. 1, pp. 106-113 (2004).
Jopling, CL. et al., Science vol. 309 pp. 1577-1581 (2005).
Henke, JI., RNA. Embo J. vol. 27, pp. 3300-3310 (2008).
Lanford RE., et al., Science vol. 327, pp. 198-201 (2010).
Krutzfeldt, J., et al., Nature vol. 438, pp. 685-689 (2005).

*Primary Examiner* — Tracy Vivlemore
*Assistant Examiner* — Kate Poliakova
(74) *Attorney, Agent, or Firm* — McDonnell Boehnen Hulbert & Berghoff LLP

(57) ABSTRACT

The present invention relates to an aptazyme comprising an aptamer for hepatitis C virus (HCV) RNA-encoding component; a hammerhead ribozyme comprising an antisense sequence to microRNA at the site released by self-cleavage; and a communication module sequence that connects the aptamer and hammerhead ribozyme and triggers a self-cleavage activity of the hammerhead ribozyme upon binding of the aptamer with the HCV RNA-encoding component. The present aptazyme inhibits microRNA activity specifically in HCV proliferating cells and thus a composition of the present invention comprising the aptazyme can be effectively used for treatment of HCV-related diseases.

4 Claims, 14 Drawing Sheets

```
#1  (1): 5'-GGGTTGGT-GTCT-GATGAGCTTT-GTCT-GATGAGCCCTT-CGCGCAATATTGT-GAGGGGCCCCCGTACGAACGTAAC-TTTGGGAAACCAAACGTAAC-ACCAAAAAAAAAAAAAAAAAA (SEQ ID NO.: 46)
#2  (2): 5'-GGGTTGGT-GTCT-GATGAGCCCTT-CGCGCAATATTGT-GAGGGGCCCCCGCGCAATAATGT-GAGGGGAAACATT-GGGAAACCAAACATT-ACCAAAAAAAAAAAAAAAAAA (SEQ ID NO.: 47)
#3  (1): 5'-GGGTTGGT-GTCT-GATGAGCCCTT-CGCGCAATATTGT-GAGGGGCCCCCGCGCAATAATGT-GAGGGGAAACATT-GGGAAACCAAACATT-ACCAAAAAAAAAAAAAAAAAA (SEQ ID NO.: 48)
#4  (1): 5'-GGGTTGGT-GTCT-GATGAGCCCTT-CGCGCAATATTGT-GAGGGGCCCCCGCACACAATATTGT-GAGGGGAAACATT-GGGAAACCAAACGTAAC-AC-ACCAAAAAAAAAAAAAAAAAA (SEQ ID NO.: 49)
#5  (1): 5'-GGGTTGGT-GTCT-GATGAGCCCTT-CGCGCAATATTGT-GAGGGGCCCCCGCTTCACCCAATATTGT-GAGGGGAAACATT-GGGAAACCAAACGTAAC-ACCAAAAAAAAAAAAAAAAAA (SEQ ID NO.: 50)
#6  (3): 5'-GGGTTGGT-GTCT-GATGAGCCCTT-CGCGCAATATTGT-GAGGGGCCCCCGCGCAATATTGT-GAGGGGAAACATT-GGGAAACCAA-CGTAAC-ACCAAAAAAAAAAAAAAAAAA (SEQ ID NO.: 51)
#7  (1): 5'-GGGTTGGT-GTCT-GATGAGCCCTT-CGCGCAATATTGT-GAGGGGCCCCCGCTGCAATATTGT-GAGGGGAAACATT-GGGAAACCAAACGTAAC-ACCAAAAAAAAAAAAAAAAAA (SEQ ID NO.: 52)
#8  (1): 5'-GGGTTGGT-GTCT-GATGAGCCCTT-CGCGCAATATTGT-GAGGGGCCCCCGCACAGCAATATTGT-GAGGGGAAA-TTTGGGAAACCAAA-G-AAC-ACCAAAAAAAAAAAAAAAA (SEQ ID NO.: 53)
#9  (1): 5'-GGGTTGGT-GTCT-GATGAGCCCTT-CGCGCAATATTGT-GAGGGGCCCCCGACACACTT-CGAAACATT-GGGAAACCAAACGTAAC-ACCAAAAAAAAAAAAAAAAAA (SEQ ID NO.: 54)
#10 (1): 5'-GGGTTGGTCGTCT-GATGAGCCCTT-CGCGCAATTGTG-AGGGGCCCCCGCGCACCCAATATT-GGGAAACATT-GGGAAACCAAACGTAAC-ACCAAAAAAAAAAAAAAAAAA (SEQ ID NO.: 55)
#11 (1): 5'-GGGTTGGT-GTCT-GATGAGCCCTT-CGCGCAATATTGT-GAGGGGCCCCCGCGC-CAATATTGT-GAGGGGAAACATT-GGGAAACCAAACGTAAC-ACCAAAAAAAAAAAAAAAAAA (SEQ ID NO.: 56)
#12 (1): 5'-GGGTTGGT-GTCT-GATGAGCCCTT-CGCGCAATATTGT-GAGGGGCCCCCGGGC-CA-CCGAAACATT-GGGAAACCAAACGTAAC-ACCAAAAAAAAAAAAAAAAAA (SEQ ID NO.: 57)
#13 (1): 5'-GGGTTGGT-GTCT-GATGAGCCCTT-CGCGCAATATTGT-GAGGGGCCCCCGCGCCCCAATATTGT-GAGGGGAAACATT-GGGAAACCAAACGTAAC-ACCAAAAAAAAAAAAAAAAAA (SEQ ID NO.: 58)
#14 (1): 5'-GGGTTGGTCGTCT-GATGAGCCCTT-CGCGCAATATTGT-GAGGGGCCCCCGCGCAATATTGT-GAGGGGAAACATT-GGGAAACCAAACGTAAC-ACCAAAAAAAAAAAAAAAAAA (SEQ ID NO.: 59)
#15 (1): 5'-GGGTTGGT-GTCT-GATGAGCCCTT-CGCGCAATATTGT-GAGGGGCCCCCCAGCCGATAC-TTTGGGAA-CCAAACCAAACGTAAC-ACCAAAAAAAAAAAAAAAAAA (SEQ ID NO.: 60)
#16 (1): 5'-GGGTTGGT-GTCT-GATGAGCCCTT-CGCGCAATATTGT-GAGGGGCCCCCGCCCCTAAC-TTTGGGAAACATT-GGGAAACCAAACGTAAC-ACCAAAAAAAAAAAAAAAAAA (SEQ ID NO.: 61)
#17 (1): 5'-GGGTTGGT-GTCT-GATGAGCCCTT-CGCGCAATATTGT-GAGGGGCCCCCGCACCGATATTGTCGAGGGGAAACATT-GGGAAACCAAACGTA-C-ACCAAAAAAAAAAAAAAAAAA (SEQ ID NO.: 62)
#18 (1): 5'-GGGTTGGT-GTCT-GATGAGCCCTT-CGCGCAATATTGT-GAGGGGCCCCCGCGCACCACCCAATATTGT-GCCAAACATT-GGGAAACCAAACGTAAC-ACCAAAAAAAAAAAAAAAAAA (SEQ ID NO.: 63)
#19 (1): 5'-GGGTTGGT-GTCT-GATGAGCCCTT-CGCGCAATATTGT-GAGGGGCCCCCGCGCACCACCACCAATATTGT-GAGGGGAAACC-TTTGGGAAACCAAACGTAAC-GTAAC-ACCAAAAAAAAAAAAAAAAAA (SEQ ID NO.: 64)
#20 (1): 5'-GGGTTGGT-GTCT-CGATGAGCTACGTCCTT-CGCGCAATATTGT-GAGGGGCCCCGCGCACCACCCAATATTGT-GAGGGGAAACATT-GGGAAACCAAACGTAAC-ACCAAAAAAAAAAAAAAAAAA (SEQ ID NO.: 65)
#21 (1): 5'-GGGTTGGT-GTCT-GATGAGTCCTT-CGCGCGAATATTGT-GAGGGGCCCCCGCACCCGAAACATT-GGGAAACCAAACGTAAC-ACCAAAAAAAAAAAAAAAAAA (SEQ ID NO.: 66)
#22 (1): 5'-GGGTTGGT-GTCT-GATGAGCCCTT-CGCGCGAATATTGT-GAGGGGCCCCCGCATGCACCACGTCCT-TTTGGGAAACCAAACGTAAC-ACCAAAAAAAAAAAAAAAAAA (SEQ ID NO.: 67)
```

Figure 10
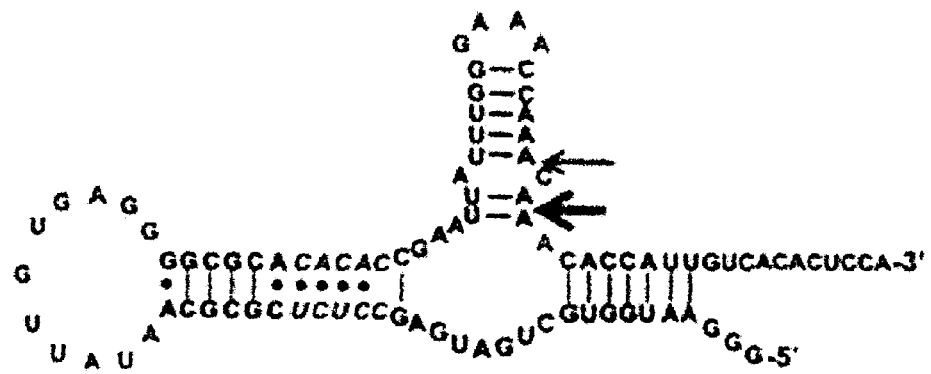
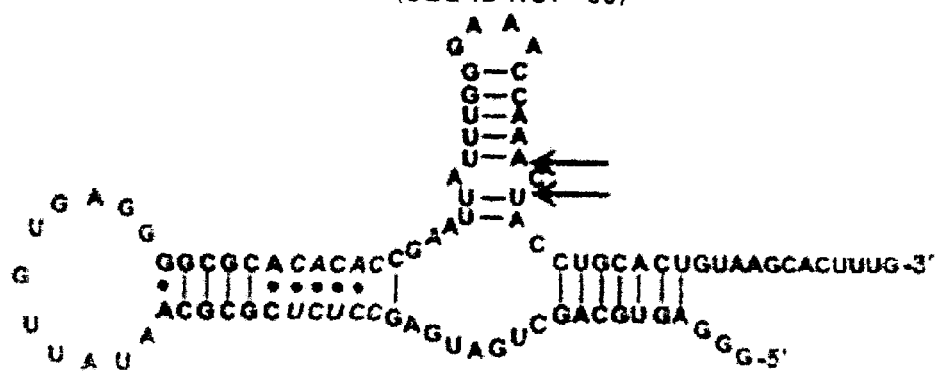

Figure 11
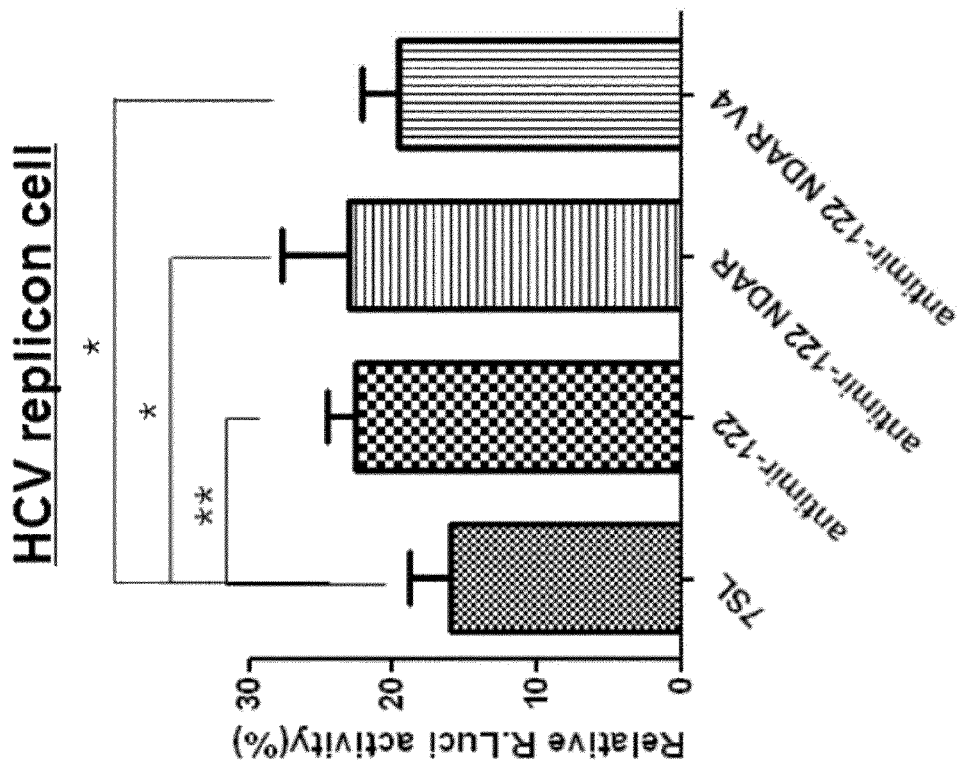
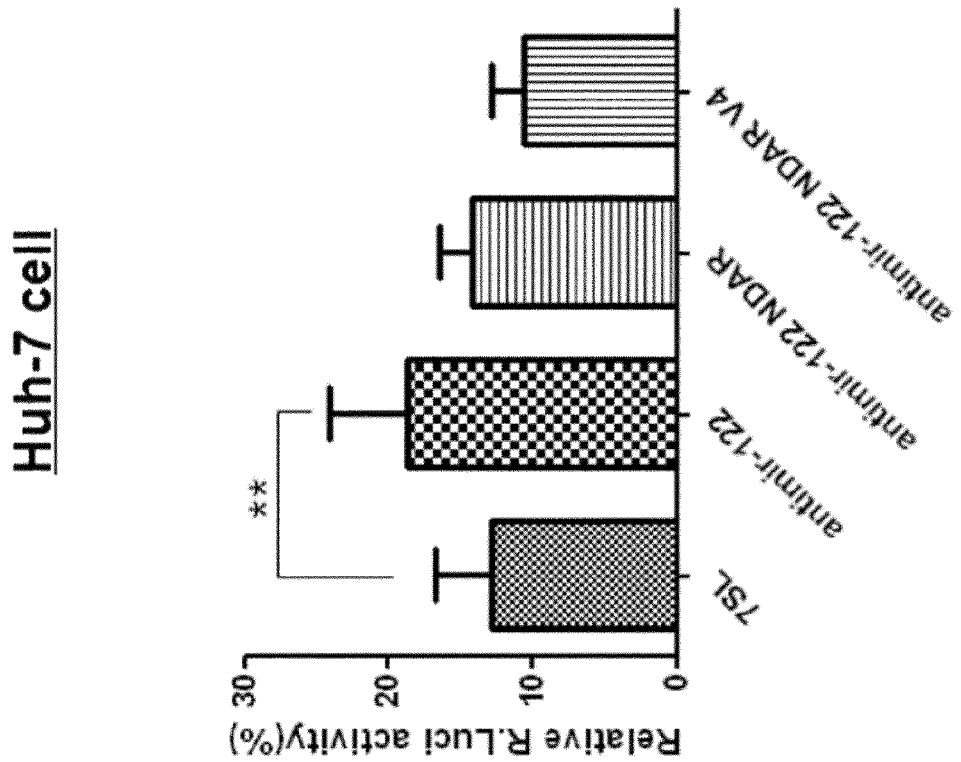

US 9,284,555 B2

SEQUENCE LISTING

```
<160> NUMBER OF SEQ ID NOS: 45

<210> SEQ ID NO 1
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide aptamer for hcv ns5b

<400> SEQUENCE: 1
gggagagcgg aagcgugcug ggccacauug ugagggggcuc agguggaucg cauggccgug      60
uccauaaccc agaggucgau ggauccu                                          87

<210> SEQ ID NO 2
<211> LENGTH: 89
<212> TYPE: RNA
<213> ORGANISM: Artificial Sequence
<220> FEATURE:
```

<223> OTHER INFORMATION: Description of Artificial Sequence: Synthetic
      oligonucleotide aptamer for hcv ns5b

<400> SEQUENCE: 2
gggagagcgg aagcgugcug ggccucgaua aaagggggccu gggauugaau cgcauggccg    60
uguccauaac ccagaggucg auggauccu                                       89

<210> SEQ ID NO 3
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide aptamer for hcv ns5b

<400> SEQUENCE: 3
gggagagcgg aagcgugcug ggccucggcu aggggggucug ggcgaaucgc auugccgugc    60
aucauaaccc agaggucgau ggauccu                                         87

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide aptamer for hcv ns5b

<400> SEQUENCE: 4
cgcgcaauau ugugaggggc gca                                             23

<210> SEQ ID NO 5
<211> LENGTH: 45
<212> TYPE: RNA
<213> ORGANISM: Artificial Sequence
<220> FEATURE:
<223> OTHER INFORMATION: Description of Artificial Sequence: Synthetic
      ribozyme oligonucleotide
<220> FEATURE:
<221> NAME/KEY: modified_base
<222> LOCATION: (1)..(6)
<223> OTHER INFORMATION: a, c, u or g
<220> FEATURE:
<221> NAME/KEY: modified_base
<222> LOCATION: (11)..(11)
<223> OTHER INFORMATION: a, c, u or g
<220> FEATURE:
<221> NAME/KEY: modified_base
<222> LOCATION: (15)..(15)
<223> OTHER INFORMATION: a, c, u or g
<220> FEATURE:
<221> NAME/KEY: modified_base
<222> LOCATION: (17)..(22)
<223> OTHER INFORMATION: a, c, u or g
<220> FEATURE:
<221> NAME/KEY: modified_base
<222> LOCATION: (24)..(24)
<223> OTHER INFORMATION: a, c, u or g
<220> FEATURE:
<221> NAME/KEY: modified_base
<222> LOCATION: (31)..(37)
<223> OTHER INFORMATION: a, c, u or g
<220> FEATURE:
<221> NAME/KEY: modified_base
<222> LOCATION: (40)..(45)
<223> OTHER INFORMATION: a, c, u or g

<400> SEQUENCE: 5
nnnnnncuga ngarncnnnn nngnygaaac nnnnnnnhhn nnnnn                      45

```
<210> SEQ ID NO 6
<211> LENGTH: 71
<212> TYPE: RNA
<213> ORGANISM: Artificial Sequence
<220> FEATURE:
<223> OTHER INFORMATION: Description of Artificial Sequence: Synthetic
      ribozyme oligonucleotide
<220> FEATURE:
<221> NAME/KEY: modified_base
<222> LOCATION: (19)..(19)
<223> OTHER INFORMATION: a, c, u or g
<220> FEATURE:
<221> NAME/KEY: modified_base
<222> LOCATION: (21)..(26)
<223> OTHER INFORMATION: a, c, u or g
<220> FEATURE:
<221> NAME/KEY: modified_base
<222> LOCATION: (28)..(28)
<223> OTHER INFORMATION: a, c, u or g

<400> SEQUENCE: 6
gggaauggug cugaugagnc nnnnnngncg aauuauuugg gaaaccaaac aaacaccauu      60
gucacacucc a                                                           71

<210> SEQ ID NO 7
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide antisense for mirna 122

<400> SEQUENCE: 7
acaaacacca uugucacacu cca                                              23

<210> SEQ ID NO 8
<211> LENGTH: 5
<212> TYPE: RNA
<213> ORGANISM: Artificial Sequence
<220> FEATURE:
<223> OTHER INFORMATION: Description of Artificial Sequence: Synthetic
      5' communication module oligonucleotide

<400> SEQUENCE: 8 ccucu                                                                   5

<210> SEQ ID NO 9
<211> LENGTH: 5
<212> TYPE: RNA
<213> ORGANISM: Artificial Sequence
<220> FEATURE:
<223> OTHER INFORMATION: Description of Artificial Sequence: Synthetic
      3' communication module oligonucleotide

<400> SEQUENCE: 9 cacac                                                                   5

<210> SEQ ID NO 10
<211> LENGTH: 5
<212> TYPE: RNA
<213> ORGANISM: Artificial Sequence
<220> FEATURE:
<223> OTHER INFORMATION: Description of Artificial Sequence: Synthetic
      3' communication module oligonucleotide

<400> SEQUENCE: 10 uccac                                                                   5
```

```
<210> SEQ ID NO 11
<211> LENGTH: 5
<212> TYPE: RNA
<213> ORGANISM: Artificial Sequence
<220> FEATURE:
<223> OTHER INFORMATION: Description of Artificial Sequence: Synthetic
      3' communication module oligonucleotide

<400> SEQUENCE: 11 ucacc                                                                      5

<210> SEQ ID NO 12
<211> LENGTH: 94
<212> TYPE: RNA
<213> ORGANISM: Artificial Sequence
<220> FEATURE:
<223> OTHER INFORMATION: Description of Artificial Sequence: Synthetic
      aptazyme oligonucleotide

<400> SEQUENCE: 12
gggaauggug cugaugagcc ucucgcgcaa uauugugagg ggcgcacaca ccgaauuauu          60
ugggaaacca aacaaacacc auugucacac ucca                                     94

<210> SEQ ID NO 13
<211> LENGTH: 95
<212> TYPE: RNA
<213> ORGANISM: Artificial Sequence
<220> FEATURE:
<223> OTHER INFORMATION: Description of Artificial Sequence: Synthetic
      aptazyme oligonucleotide

<400> SEQUENCE: 13
gggaguuggu gcugaugagc cucucgcgca auauugugag gggcgcacac accgaauuau          60
uugggaaacc aaacaaacac cauugucaca cucca                                    95

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(20)
<223> OTHER INFORMATION: a, c, t or g

<400> SEQUENCE: 14
ttggtgtctg atgagnnnnn cgcgccatat tgtgaggggc gcg                           43

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(30)
<223> OTHER INFORMATION: a, c, t or g

<400> SEQUENCE: 15
tacgtttggt ttcccaaacg tttcgnnnnn cgcgcccctc acaat                         45

<210> SEQ ID NO 16
<211> LENGTH: 37
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtaatacga ctcactatag ggttggtgtc tgatgag                          37

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttttttttt tttttggtg ttacgtttgg tttcccaaa                        39

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgcgtcgac gggaatggtg ctgatgag                                   28

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctctagatg gagtgtgaca atggtg                                     26

<210> SEQ ID NO 20
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccgctcgaga caaacaccat tgtcacactc caccggacaa acaccattgt cacactc   57

<210> SEQ ID NO 21
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cactagttgg agtgtgacaa tggtgtttgt ccggtggagt gtgacaatgg tgtttg    56

<210> SEQ ID NO 22
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      anti-dicer star for mirna 122, sense
      oligonucleotide

<400> SEQUENCE: 22
tcgactgata atggcgtttg atagtttaga t                                    31

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      anti-dicer star for mirna 122, antisense
      oligonucleotide

<400> SEQUENCE: 23
ctagatctaa actatcaaac gccattatca g                                    31

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      anti-mirna dicer for mirna 122, sense
      oligonucleotide

<400> SEQUENCE: 24
tcgactttga tagtttagac acaaacacca tt                                   32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      anti-mirna dicer for mirna 122, antisense
      oligonucleotide

<400> SEQUENCE: 25
ctagaatggt gtttgtgtct aaactatcaa ag                                   32

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      anti-drosha star for mirna 122, sense
      oligonucleotide

<400> SEQUENCE: 26
tcgaccctag cagtagctat ttagtgtgat                                      30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      anti-drosha star for mirna 122, antisense
      oligonucleotide

<400> SEQUENCE: 27
ctagatcaca ctaaatagct actgctaggg                                      30
```

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      anti-mirna drosha for mirna 122, sense
      oligonucleotide

<400> SEQUENCE: 28
tcgactgtca cactccacag ctctgctat                                    29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      anti-mirna drosha for mirna 122, antisense
      oligonucleotide

<400> SEQUENCE: 29
ctagatagca gagctgtgga gtgtgacag                                    29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      anti-mature mirna for mirna 122, sense
      oligonucleotide

<400> SEQUENCE: 30
tcgacacaaa caccattgtc acactccat                                    29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      anti-mature mirna for mirna 122, antisense
      oligonucleotide

<400> SEQUENCE: 31
ctagatggag tgtgacaatg gtgtttgtg                                    29

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      anti-mirna drosha for mirna 17-5p, sense
      oligonucleotide

<400> SEQUENCE: 32
tcgacgtaag cactttgaca ttattctgat                                   30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      anti-mirna drosha for mirna 17-5p, antisense oligonucleotide

<400> SEQUENCE: 33
ctagatcaga ataatgtcaa agtgcttacg                                           30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      anti-mature mirna for mirna 17-5p, sense
      oligonucleotide

<400> SEQUENCE: 34
tcgacactac ctgcactgta agcactttgt                                           30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      anti-mature mirna for mirna 17-5p, antisense
      oligonucleotide

<400> SEQUENCE: 35
ctagacaaag tgcttacagt gcaggtagtg                                           30

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgcgtcgac gggagtgcag ctgatgag                                             28

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gctctagaca aagtgcttac agtgcag                                              27

<210> SEQ ID NO 38
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (57)..(57)
<223> OTHER INFORMATION: a, c, t or g

<400> SEQUENCE: 38
aagcagtggt atcaacgcag agtactttt tttttttttt tttttttttt tttttvn              57

<210> SEQ ID NO 39

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
taatacgact cactataggg aatggtgctg                           30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
taatacgact cactataggg agtgcagctg                           30

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
aagcagtggt atcaacgcag agt                                  23

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
cgtaacacca acgggcgcgc catg                                 24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ctcgtcctgc agttcattca gggc                                 24

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gtaacccgtt gaacccccatt                                     20

<210> SEQ ID NO 45
<211> LENGTH: 20

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccatccaatc ggtagtagcg                                                20
```

APTAZYME CAPABLE OF SELECTIVE SILENCING OF TARGET MIRNA BY RELEASING AN ANTISENSE SEQUENCE IN HEPATITIS C VIRUS-INFECTED CELLS AND USE THEREOF

Aptazyme capable of selective silencing of target miRNA by releasing an antisense sequence in Hepatitis C virus-infected cells and use thereof

CROSS-REFERENCE TO RELATED APPLICATIONS

This application is a national stage application of International Patent Application No. PCT/KR2011/006856, filed on Sep. 16, 2011, which claims the benefit of priority of Korean Patent Application No. 10-2010-0091145, filed on Sep. 16, 2010. The entire content of each of these applications is hereby incorporated by reference.

SEQUENCE LISTING

The instant application contains a Sequence Listing which has been submitted electronically in ASCII format and is hereby incorporated by reference in its entirety. Said ASCII copy, created on Dec. 4, 2014, is named 23NN-177173_SL.txt and is 13,159 bytes in size.

TECHNICAL FIELD

The present invention relates to an aptazyme capable of selective silencing of target miRNA by releasing an antisense sequence in Hepatitis C virus-infected cells and use thereof.

BACKGROUND ART

Hepatitis C virus (HCV) is a positive-sense single-stranded RNA virus belonging to the family Flaviviridae. HCV is the cause of non-A, non-B hepatitis (Kuo, G., et al., 1989, Science 244, 362-364), and when the HCV infection develops into chronic hepatitis, it can lead to liver cirrhosis or liver cancer with a high mortality rate (Saito, I., et al., 1990, Proc. Natl Acad. Sci. USA 87, 6547-6549). About 1 to 2% of the total population in the world is infected with hepatitis C virus. However, since HCV is present in the body with a very low titer, it is hard to diagnose HCV infection. Furthermore, an effective drug or vaccine for targeting HCV virus has not been developed yet.

Recently, a use of α-interferon that is partly effective against HCV-related diseases by suppressing HCV proliferation and co-administration of the α-interferon and ribavirin are available for treatment of HCV infection. However, it has been reported that effects of these methods vary among different virus strains and they remain to be effective for only 50% of the HCV-infected patients (Bartenschlager R, Frese M, Pietschmann T. Novel insights into hepatitis C virus replication and persistence. Adv Virus Res 2004, 63, 71-180).

When the viral components are targeted for HCV treatment, this often leads to the emergence of HCV escape mutants. Thus targeting host factors instead has emerged as an alternative strategy to HCV treatment.

MicroRNAs (miRNAs) are endogenous, small non-coding RNAs that function to repress cellular gene expression in a sequence-specific manner, generally through translational repression or degradation of target mRNAs (Chekulaeva M, Filipowicz W. Mechanisms of miRNA-mediated post-translational regulation in animal cells. Curr Opin Cell Biol 2009, 21, 452-460). MicroRNA 122 (miR-122) is the most abundant miRNA in the liver among others (Chang J., et al., miR-122, a mammalian liver-specific microRNA, is processed from her mRNA and may down-regulate the high affinity cationic amino acid transporter. RNA Biol 2004, 1, 106-113) and it is known to promote HCV replication by interacting with the 5' untranslated region (UTR) of the viral genome (Jopling C L., et al., Modulation of hepatitis C virus RNA abundance by a liver-specific microRNA. Science 2005, 309, 1577-1581; Henke J I., et al., microRNA-122 stimulates translation of hepatitis C virus RNA. EMBO J 2008, 27, 3300-3310 etc.).

In the recent study, it has been reported that when the HCV-infected chimpanzees were treated with the antisense oligonucleotide against miR-122, HCV proliferation could be suppressed (Lanford R E., et al., Therapeutic silencing of microRNA-122 in primates with chronic hepatitis C virus infection. Science 2010, 327, 198-201). However, microRNA plays an important role in regulating the expression of a large number of genes involved in cellular physiological function including lipid metabolism (Krutzfeldt J., et al. Silencing of microRNAs in vivo with 'anagomir'. Nature 2005, 438, 685-689). Therefore, the non-selective silencing of microRNA-122 independent of cell types is highly likely to cause side effects due to the gene modification of the genes that are critical for the cellular physiological activity.

Therefore, there is a high demand for the development of a silencing system that can inhibit the microRNA-122 activity selectively in HCV-replicating cells but not in normal liver cells.

In this regard, the present inventors have developed an aptazyme that is capable of releasing the antisense sequence to microRNA by specifically responding to the HCV RNA-encoding component in order to inhibit microRNA activity specifically in HCV-replicating cells, thereby completing the present invention.

DISCLOSURE

Technical Problem

The object of the present invention is to provide an aptazyme that binds and deactivates a HCV RNA-encoding component specifically in HCV-infected cells and simultaneously releases an antisense sequence to the microRNA inhibiting its activity.

Another object of the present invention is to provide a composition for treatment of HCV-related diseases, comprising the aptazyme that binds and deactivates the HCV RNA-encoding component specifically in HCV-infected cells and simultaneously releases an antisense sequence to the microRNA inhibiting its activity and a method of treatment using the same.

Still another object of the present invention is to provide a method for preparing the aptazyme that binds and deactivates the HCV RNA-encoding component specifically in HCV-infected cells and simultaneously releases an antisense sequence to the microRNA inhibiting its activity.

Technical Solution

As one aspect to achieve the above objects, the present invention provides an aptazyme that releases an antisense sequence to microRNA specifically in HCV-infected cells, comprising i) an aptamer for hepatitis C virus (HCV) RNA-encoding component; ii) a hammerhead ribozyme comprising an antisense sequence to microRNA at the site released by self-cleavage; and iii) a communication module sequence that connects the aptamer and hammerhead ribozyme and induces a self-cleavage activity of the hammerhead ribozyme upon binding of the aptamer with the HCV RNA-encoding component.

HCV RNA which is a genome of HCV is translated into a single protein complex composed of about 3000 amino acids, which is then cleaved by proteases of the host cell and virus into several structural proteins such as C, E1, and E2, and non-structural proteins such as NS2, NS3, NS4A, NS4B, NS5A, and NS5B. Among the HCV non-structural proteins, NS5B is a RNA-dependent RNA polymerase which is a critical factor in HCV proliferation and thus its activity demonstrates the state of HCV proliferation in the cells.

As used herein, the term 'HCV RNA-encoding component' refers to a protein or peptide that demonstrates the proliferation of HCV in the cells like the structural and non-structural HCV proteins.

As used herein, the term 'aptazyme' may be used interchangeably with the term 'allosteric ribozyme'. Also, microRNA may be used interchangeably with 'miRNA' and 'mir'. 'Antisense sequence to microRNA' can be used interchangeably with 'antimir'. An aptamer for a HCV RNA-encoding component of the present invention binds with a high affinity to one of the proteins including the structural proteins such as C, E1, E2, and non-structural proteins such as NS2, NS3, NS4, NS4A, NS4B, NS5 and NS5A, and hence deactivating its activity, more preferably it could be an aptamer binding specifically to HCV NS5B protein.

An aptamer for NS5B of the present invention is a substance selected by the present inventors using Systematic Evolution of Ligands of Exponential (SELEX) enrichment, comprising the following sequence.

1. Aptamer RNA Sequence (SEQ ID NO. 1)

GGGAGAGCGGAAGCGUGCUGGGCCACAUUGUGAGGGGCUCAGGUGGAUCG

CAUGGCCGUGUCCAUAACCCAGAGGUCGAUGGAUCCU

2. Aptamer RNA Sequence (SEQ ID NO. 2)

GGGAGAGCGGAAGCGUGCUGGGCCUCGAUAAAAGGGGCCUGGGAUUGAAU

CGCAUGGCCGUGUCCAUAACCCAGAGGUCGAUGGAUCCU

3. Aptamer RNA Sequence (SEQ ID NO. 3)

GGGAGAGCGGAAGCGUGCUGGGCCUCGGCUAGGGGGUCUGGGCGAAUCGC

AUUGCCGUGCAUCAUAACCCAGAGGUCGAUGGAUCCU

4. Aptamer RNA Sequence (SEQ ID NO. 4)

CGCGCAAUAUUGUGAGGGCGCA

As used herein, 'communication module sequence' refers to a sequence connecting the aptamer and the hammerhead ribozyme. If the aptamer is bound with the HCV RNA-encoding component, the self-cleavage activity of the hammerhead ribozyme can be triggered.

The present invention provides an aptazyme that is prepared by connecting an aptamer that binds specifically to HCV RNA-encoding protein and a hammerhead ribozyme via communication module and that can allosterically regulate the activity of its hammerhead ribozyme domain. Hence the present aptazyme system can trigger self-cleavage activity of hammerhead ribozyme selectively in HCV-replicating cells. Furthermore, the self-cleaved ribozyme releases an antisense sequence to microRNA that is essential for HCV proliferation, only in HCV-replicating cells, and thus it can suppress HCV proliferation effectively and selectively.

The sequence of the released part of the self-cleaved hammerhead ribozyme is replaced by the antisense sequence to microRNA, preferably the antisense sequence to microRNA-122. Therefore, the hammerhead ribozyme of the present invention self-cleaves selectively in HCV-replicating cells and releases the antisense sequence to microRNA, thereby suppressing microRNA activity and ultimately the HCV proliferation.

The hammerhead ribozyme of the present invention comprises the below-specified RNA sequence, but is not limited thereto, and it may have the sequence structure shown in FIG. 1. FIG. 1 shows the consensus nucleotide sequence and structure of hammerhead ribozyme, and the mark •(N) represents A, U, C or G nucleotides, while R represents purine, Y represents pyrimidine, and h represents A, U, or C. The underlined part of the below sequence represents the part of hammerhead ribozyme sequence replaced by the antisense sequence to microRNA-122 and 'N' represents any nucleotide including A, C, G, and U.

Meanwhile, when the antisense sequence to microRNA is inserted into the hammerhead ribozyme, it is preferable to avoid inserting into the catalytic core region (italicized sequence of SEQ ID Nos.5 and 6). In addition, it is preferable to avoid inserting into the consensus nucleotide sequence of FIG. 1 which represents catalytic core region of the hammerhead ribozyme.

1. RNA Sequence of Hammerhead Ribozyme (SEQ ID No. 5)

NNNNNN*CUGANGARNC*NNNNNNN*GN YGAAA C*NNNNNNNhhNNNNNN

2. RNA Sequence of Hammerhead Ribozyme (SEQ ID No. 6)

GGGAAUGGUG*CUGAUGAGN C*NNNNNNN*GN CGAAUUAUUUGGGAA*<u>ACCAAAC</u>

<u>AAACACCAUUGUCACACUCCA</u>

The antisense sequence to microRNA-122 that is released by self-cleavage of the present hammerhead ribozyme comprises the following sequence.

Antisense Sequence to MicroRNA-122 (SEQ ID No. 7)
ACAAACACCAUUGUCACACUCCA

A communication module sequence connects an aptamer and hammerhead ribozyme. Binding of a protein (ligand) to the aptamer of aptazyme of the present invention leads to a structural change in the aptamer and hammerhead ribozyme that are connected by the communication module sequence, which then activates self-cleavage activity of hammerhead ribozyme, resulting in the specific release of an antisense sequence to microRNA.

The communication module of the present invention can be selected via SELEX enrichment method. To be specific, in order to identify effective communication module sequence of ribozyme, the candidate sequences for communication module are first designated as NNNNN, and then random sequences are generated with the equimolar incorporation of A, T, C, G at each N position. Then, the aptazyme library is prepared having each aptazyme comprising i) an aptamer for HCV NS5B protein, ii) a hammerhead ribozyme and iii) communication module. The prepared aptazyme library is mixed with NS5B proteins and other proteins, and then RNA pools that show HCV NS5B-dependent self-cleavage activity are isolated. The isolated RNA pools are further analyzed to identify their communication module sequences by sequencing analysis.

The communication module sequences selected by the above method vary depending on the aptazymes selected in the present invention, but preferably 5' communication module sequence is 'CCTCT', and 3' communication module sequence is 'CACAC', 'TCCAC', or 'TCACC'.

Therefore, the communication module sequence of the present invention comprises the CCUCU (SEQ ID No. 8) as 5' communication module sequence, and the CACAC(SEQ ID No. 9), UCCAC(SEQ ID No. 10) or UCACC(SEQ ID No. 11) as 3' communication module sequence.

The HCV NS5B-dependent aptazyme of the present invention that releases an antisense sequence to microRNA-122 comprises the below-specified RNA sequence, but is not limited thereto. The present aptazyme may have the 5'-NCNNNNNNGN-3' part of stem II substituted with the 5' communication module sequence-aptamer sequence-3' communication module sequence in the ribozyme having a sequence structure of FIG. 1.

The underlined part of the following sequence represents a communication module, the italicized sequence represents an aptamer for HCV NS5B, and the bold part represents an antisense sequence to microRNA-122.

1. Sequence of Aptazyme (SEQ ID NO. 12)

GGGAAUGGUGCUGAUGAG<u>CCUCU</u>*CGCGCAAUAUUGUGAGGGGCGCA*

<u>CACAC</u>CGAAUUAUUGGGAAACCAAACAAACACCAUUGUCACACUCCA

2. Sequence of Aptazyme (SEQ ID NO. 13)

GGGAGUUGGUGCUGAUGAG<u>CCUCU</u>*CGCGCAAUAUUGUGAGGGGCGCA*

<u>CACAC</u>CGAAUUAUUUGGGAAACCAAACAACAAACACCAUUGUCACACU

CCA

As another aspect, the present invention provides a composition for treatment of HCV-related diseases, comprising an aptazyme that comprises (i) an aptamer for HCV RNA-encoding component; (ii) hammerhead ribozyme comprising an antisense sequence to microRNA at the site released by self-cleavage; and (iii) a communication module sequence that connects the aptamer and hammerhead ribozyme and triggers the self-cleavage activity of the hammerhead ribozyme upon binding of the aptamer with HCV RNA-encoding component.

As still another aspect, the present invention provides a use of the aptazyme for the treatment of HCV-related diseases.

The HCV-related diseases are caused by HCV that induces hepatitis, liver fibrosis, liver cirrhosis, and liver cancer.

As another aspect, the present invention provides a method for treatment of HCV-related diseases comprising the step of administering the composition for HCV treatment to HCV carriers or subjects with hepatitis, liver fibrosis, liver cirrhosis, or liver cancer caused by HCV.

According to one specific Example of the present invention, in the aptazyme of the present invention, the aptamer binds specifically to HCV RNA-encoding component (Example: HCV NS5B protein) suppressing the NS5B activity, and simultaneously this binding triggers the self-cleavage activity of hammerhead ribozyme, which then releases an antisense to microRNA-122. Therefore, the present aptazyme is effective in inhibiting HCV proliferation selectively in HCV-infected cells (refer to Example 4). Therefore, a composition comprising the aptazyme of the present invention can be effectively used for the treatment of HCV-related diseases.

As used herein, the term 'treatment' means all of the actions in which the symptoms of the HCV-related diseases is relieved or improved by administration of the composition and the term 'subject' refers to all types of animals having HCV-related diseases including humans.

The composition may be administered via any of the common routes, as long as it can reach the target tissue of the body. Thus, the composition of the present invention may be administered by intraperitoneal, intravenous, intramuscular, subcutaneous, intradermal, intranasal, intrapulmonary, intrahepatic, or intrarectal route depending on the case, but is not limited thereto. Also, the composition may be administered by arbitrary apparatus that can deliver the active ingredients to a target cell.

The composition of the present invention for treatment may be administered in a pharmaceutically effective amount. The term 'pharmaceutically effective amount' refers to the dose that is applicable and sufficient for medical treatment of the diseases with reasonable benefit/risk ratio. Further, the range of effective amount is determined by the factors including the subject type and severity of disease, age, sex, drug mechanism, sensitivity to drug, duration of drug administration, route for administration, excretion rate, period of treatment, and the type of drug co-administered, and other factors well-known in the medical field.

Furthermore, the composition of the present invention can be used solely, or together with other methods such as surgery, hormone treatment, drug treatment, and biologic response modifier for treatment of HCV-related diseases.

As another aspect, the present invention provides a method for preparing the aptazyme that releases an antisense sequence to microRNA selectively in HCV-infected cells.

To be specific, the preparation method may comprise the steps of, (a) performing PCR using a primer set of SEQ ID Nos. 14 (5' primer: 5'-TTGGTGTCTGATGAGNN NNNCGCGCCATATTGTGAGGGGCGCG-3', where N represents nucleotide with the equimolar incorporation of G, A, T, C at each position) and 15 (3' primer: 5'-TACGTTTGGT TTCCCAAACGTTTCGNNNNNCGCGCCCCTCACAAT-3', where N represents nucleotide with the equimolar incorporation of G, A, T, C at each position) which comprise five random sequences in a communication module and a Taq polymerase; (b) performing subsequent PCR by adding a primer set of SEQ ID Nos. 16 (5' primer: 5'-GGTAATACG ACTCACTATAGGGTTGGTGTCTGATGAG-3') and 17 (3' primer: 5'-TTTTTTTT TTTTTTTTGGTGTTACGTTTG-GTTTCCCAAA-3') and a Taq polymerase to the PCR products of step (a); (c) preparing an aptazyme library by in vitro transcription of the PCR products of step (b) using T7 polymerase, (d) mixing the aptazyme library with NS5B protein and other proteins and selecting the RNA pools that get self-cleaved specifically in the presence of NS5B protein, and then obtaining DNA by performing RT-PCR for each of the isolated aptazyme RNA pools; (e) performing PCR by adding a primer set of SEQ ID Nos. 18 (5' primer: 5'-ACGCGTC-GACGGGAATGGTGCTGATGAG) and 19 (3' primer: 5'-GCTCTAGATGGAGTGTGACAATGGTG) and a Taq polymerase to the aptazyme DNAs of step (d), and (f) performing in vitro transcription of the PCR product of step (e).

The aptazymes prepared by the above method can be self-cleaved only in the presence of HCV RNA-encoding component (example: HCV NS5B protein) and subsequently release an antisense sequence to microRNA-122, and hence it can suppress HCV proliferation selectively in HCV-infected cells.

Advantageous Effects

The aptazyme of the present invention does not inhibit the microRNA activity in normal cells but selectively in the HCV-infected cells. Thus it can be effectively used for treatment of HCV-related diseases. In addition, the present aptazyme can suppress viral protein function through having a domain specifically binding to the viral proteins, and simultaneously inhibit the microRNA activity, thereby treating HCV-related diseases effectively and specifically.

DESCRIPTION OF DRAWINGS

FIG. 7 is a schematic diagram of the NS5B-dependent aptazyme.

FIG. 8 is a diagram showing the sequence of the selected NS5B-dependent aptazyme. The sequence of twenty-two different RNAs among 25 different ribozyme clones are shown. Numbers in parentheses represents the number of clones found repeatedly.

FIG. 10 is a diagram showing the sequence and expected secondary structure of antimir-122 NDAR (A) and antimir-17-5p NDAR (B). The italicized sequence represents the communication module sequence while the arrow represents self-cleavage site.

FIG. 11 demonstrates the selective inhibition of miRNA-122 activity by antimir-122 NDAR in the HCV replicon cells.

BEST MODE

Mode for Invention

Hereinafter, the present invention is described in more detail through providing Examples and Experimental Examples as below. However, these Examples are merely meant to illustrate, but in no way to limit, the claimed invention.

Example 1

Cell Culture

HCV genotype 1b subgenomic replicon construct, pFK-I389neo/NS3-3'/5.1 was provided by Dr. R. Bartenschlager (Univ. of Heidelberg, Germany). HCV replicon RNA was synthesized by in vitro transcription with the AseI and ScaI-digested replicon plasmid (Hwang B., et al, Isolation of specific and high-affinity RNA aptamers against NS3 helicase domain of hepatitis C virus. RNA, 2004, 10, 1277-1290 etc.). Huh-7 human hepatoma cell line was purchased from American Type Culture Collection (ATCC) and was cultured in Dulbecco's modified Eagle medium (DMEM) (Invitrogen) with 10% fetal bovine serum (FBS). Huh-7 cells highly express miR-122 and thus can be used to confirm HCV replication. Huh-7 cells were electrophoretically transfected with the HCV replicon RNA using conditions of 950 µF and 250V with a gene pulser system (Bio-Rad) and were cultured in the presence of 500 µg/ml G418(Invitrogen) to isolate a stable HCV replicon cell line.

Example 2

Figure 1:
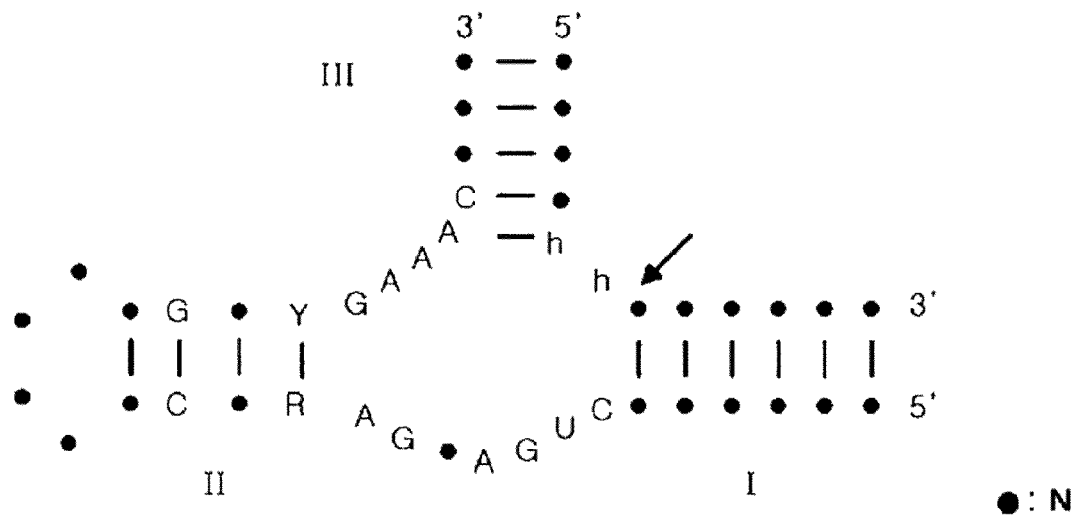
FIG. 1 is a diagram showing the sequence and structure of a hammerhead ribozyme.
Figure 2:
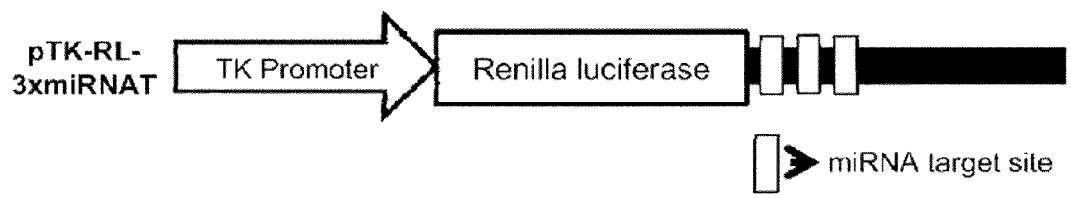
FIG. 2 is a diagram showing the pTK-RL-3×miR122T reporter construct.

Evaluation of Anti-miRNA-122 Expression Vector for Inhibition of miRNA 122 Activity 2-1. Reporter Construct for Evaluation of Anti-miRNA Activity A reporter construct whose expression can be down-regulated in miR-122 harboring naive Huh-7 and HCV replicon Huh-7 cells was created by inserting three copies of target sequence against miR-122 (5'-CAAACACCATTGTCA-CACTCCA) into the 3'-UTR of a pTK-RL vector encoding Renilla luciferase under HSVtk promoter as described below (refer to FIG. 2).

First, PCR was performed with primers (5'-CCGCTC-GAGACAAACACCATTGTCACACTCCAC-CGGACAAACACCATTGTCACACTC, SEQ ID No. 20; 5'-CACTAGTTGGAGTGTGACAATGGT-GTTTGTCCGGTGGAGTGTGACAATGGTGTTTG, SEQ ID No. 21), and the amplified DNA was cloned into the XhoI and SpeI site of pTK-RL (hereinafter, refer to this final construct as pTK-RL-3×miR122T).

As controls, reporter constructs lacking a target sequence against miRNA(MCS) and reporter constructs with three copies of the target sequence against miR-17-5p or let-7a were produced (refer to as pTK-RL-3×miR-17-5p and pTK-RL-3×miRlet-7aT respectively). A cytomegalovirus (CMV) promoter-driven firefly luciferase gene construct (pCMV-F.luci) was used as an internal control (hereinafter, refer to as pCMV-F. luci).

2-2. Construction of Expression Vector Encoding Anti-miRNA

Figure 3:
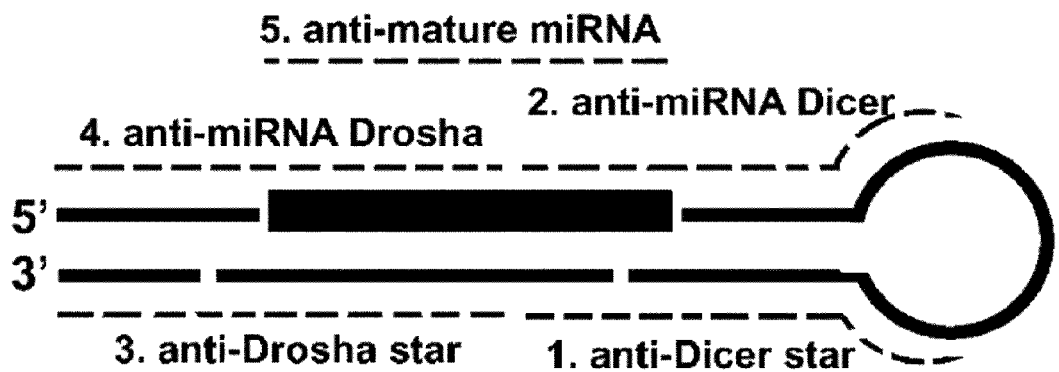
FIG. 3 is a diagram showing various target position in microRNA precursor for anti-miRNA. The box part represents the target position in mature miRNA.

To construct expression vectors encoding antisense sequence targeting diverse regions of miR-122 or miR-17-5p, the below sense and antisense oligonucleotides were synthesized (Bioneer, Korea), hybridized, and cloned into the SalI and XbaI site of U6+1 snRNA promoter or 7SL RNA promoter-driven expression cassettes which were obtained from Dr. DR. Engelke (Univ. of Michigan). Each target site is shown in FIG. 3.

<Anti-miRNA 122>

(1) anti-Dicer star (targeting the Dicer processing site and part of the miRNA passenger strand)

```
5'-TCGACTGATAATGGCGTTTGATAGTTTAGAT (sense,
SEQ ID No. 22)

5'-CTAGATCTAAACTATCAAACGCCATTATCAG (antisense,
SEQ ID No. 23)
```

(2) anti-miRNA Dicer (targeting the Dicer processing site and part of the mature miRNA)

```
5'-TCGACTTTGATAGTTTAGACACAAACACCATT (sense,
SEQ ID No. 24)

5'-CTAGAATGGTGTTTGTGTCTAAACTATCAAAG (antisense,
SEQ ID No. 25)
```

(3) anti-Drosha star (targeting the Drosha processing site and part of the miRNA passenger strand)

```
5'-TCGACCCTAGCAGTAGCTATTTAGTGTGAT (sense,
SEQ ID No. 26)

5'-CTAGATCACACTAAATAGCTACTGCTAGGG (antisense,
SEQ ID No. 27)
```

(4) anti-miRNA Drosha (targeting the Drosha processing site and part of the mature miRNA)

```
5'-TCGACTGTCACACTCCACAGCTCTGCTAT (sense,
SEQ ID No. 28)

5'-CTAGATAGCAGAGCTGTGGAGTGTGACAG (antisense,
SEQ ID No. 29)
```

(5) anti-mature miRNA (targeting the mature miRNA)

```
5'-TCGACACAAACACCATTGTCACACTCCAT (sense,
SEQ ID No. 30)

5'-CTAGATGGAGTGTGACAATGGTGTTTGTG (antisense,
SEQ ID No. 31)
```

<Anti-miRNA 17-5p>

(1) anti-miRNA Drosha (targeting the Drosha processing site and part of the mature miRNA)

```
5'-TCGACGTAAGCACTTTGACATTATTCTGAT (sense,
SEQ ID No. 32)

5'-CTAGATCAGAATAATGTCAAAGTGCTTACG (antisense,
SEQ ID No. 33)
```

(2) anti-mature miRNA (targeting mature miRNA)

```
5'-TCGACACTACCTGCACTGTAAGCACTTTGT (sense,
SEQ ID No. 34)

5'-CTAGACAAAGTGCTTACAGTGCAGGTAGTG (antisense,
SEQ ID No. 35)
```

2-3. Anti-miRNA Reporter Assay

To evaluate anti-miRNA activity of anti-miRNA expression vectors, 25 ng pCMV-F.luci and 100 ng pTK-RL-3×miR122T or pTK-RL-3×miR-17-5pT were cotransfected with 7SL- or U6+1-based anti-miRNA expression vector (400 ng) into Huh-7 and HCV replicon Huh-7 cells. After 24 hours of transfection, the cells were harvested and lysed, and reporter gene expression activities were determined by measuring relative light units using a TD-20/20 luminometer (Turner Designs Instrument) and dual-luciferase reporter assay system (Promega).

Figure 4:
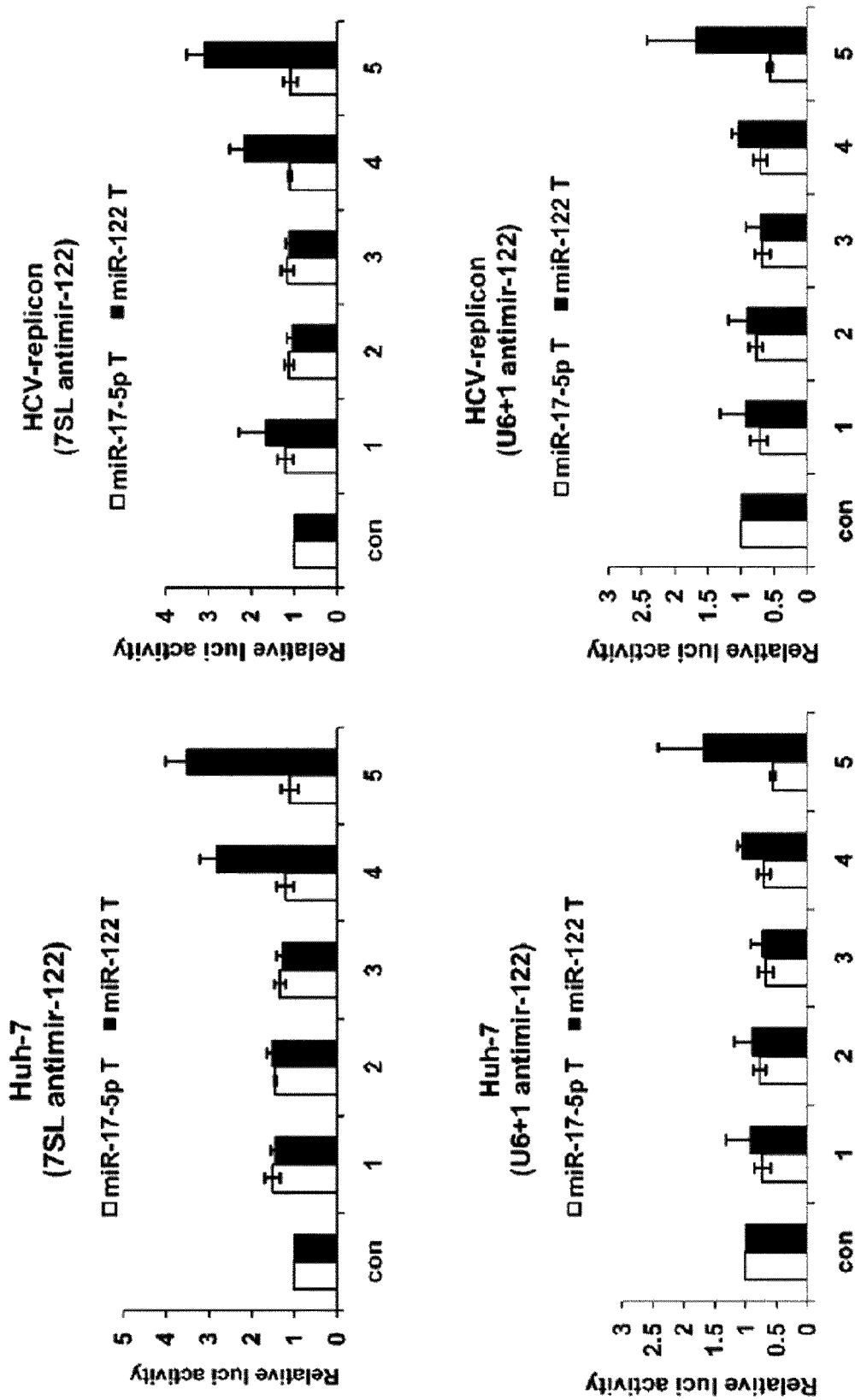
FIG. 4 is a graph demonstrating inhibition of microRNA activity by anti-miRNA targeting different parts of microRNA: anti-Dicer star (lane 1), anti-miRNA Dicer (lane 2), anti-Drosha star (lane 3), anti-miRNA Drosha (lane 4), anti-mature miRNA (lane 5).

FIG. 4 shows that when pTK-RL-3×miR122T reporter construct was cotransfected with the expression vector encoding anti-Dicer star (1 lane), anti-miRNA Dicer (2 lane), or anti-Drosha star (3 lane), no derepression of reporter activity was evident in pTK-RL-3×miR122T reporter construct. However, when the pTK-RL-3×miR122T reporter construct was cotransfected with expression vectors for either anti-miRNA Drosha (4 lane) or anti-mature miRNA (5 lane), the reporter activity was derepressed in both Huh-7 and HCV replicon Huh-7 cells. These results indicate non-specific inhibition of miRNA-122 activity regardless of HCV proliferation.

Furthermore, when pTK-RL-3×miR-17-5p reporter construct was cotransfected with each of the antimiR-122 expression vectors, the reporter activity was not derepressed. This result indicates that derepression of reporter activity by anti-mir-122 expression vector results from specific targeting of miR-122. Taken together, the intracellular expression of an antisense sequence targeting full or seed sequence of mature miR-122 could efficiently and specifically inhibit miR-122 activity.

Figure 5:
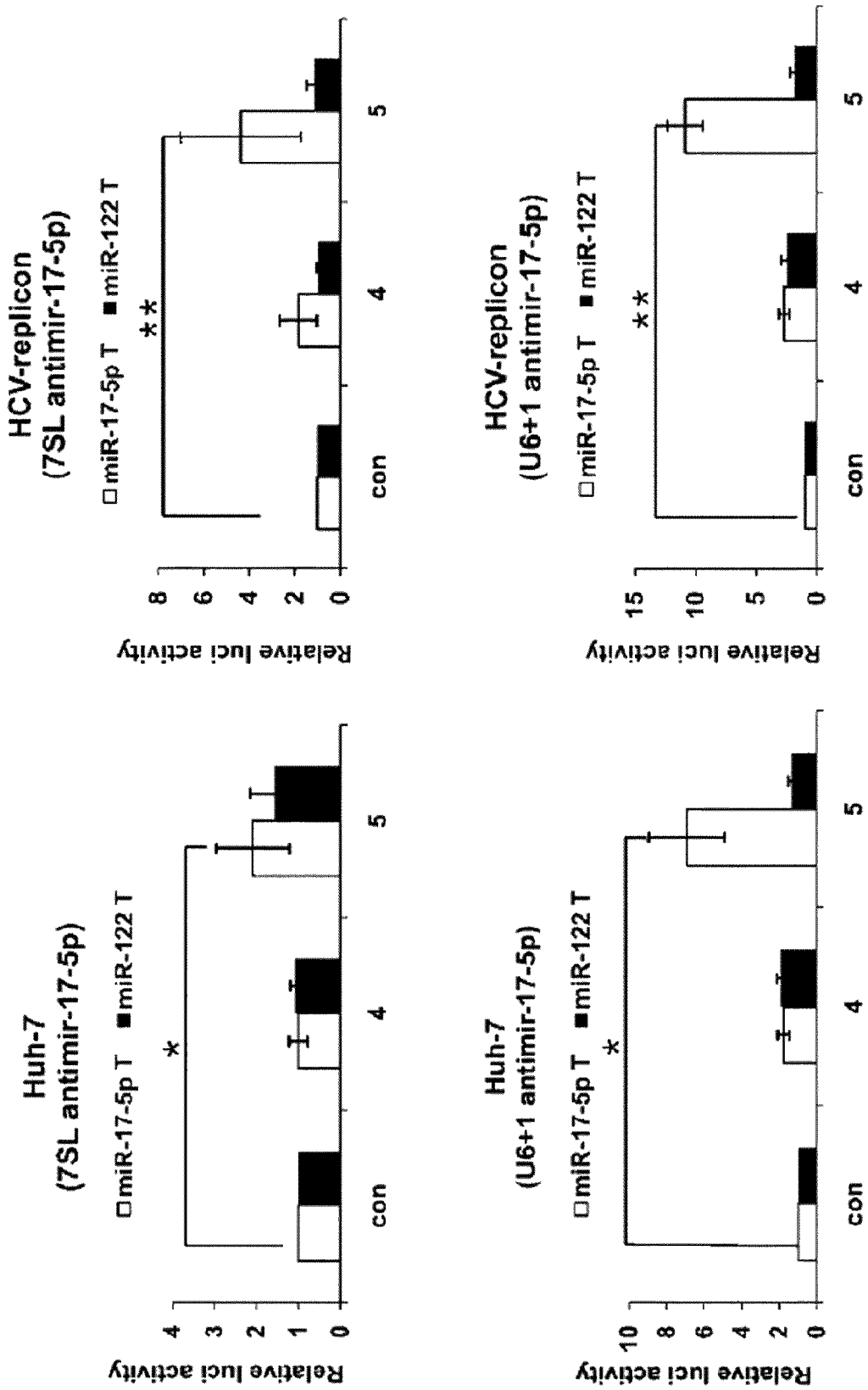
FIG. 5 shows the regulatory effect of anti-miRNA by miR-17-5P activity (lane 4: anti-miRNA Drosha, lane 5: anti-mature miRNA).

FIG. 5 demonstrates the regulatory effect of anti-miRNA upon miR-17-5p derepression. Cells were transfected with a miR-17-5pT or miR122T as control vector (con lane) alone or together with 7SL- or U6+1-based expression vector encoding anti-miR-17-5p (lane 4: anti-miRNA Drosha, lane 5: anti-mature miRNA). Intracellular expression of an antisense sequence targeting the full region of mature miR-17-5p effectively and specifically inhibited miR-17-5p activity. Specific anti-miR-17-5p activity was observed in both Huh-7 and HCV replicon Huh-7 cells.

Figure 6:
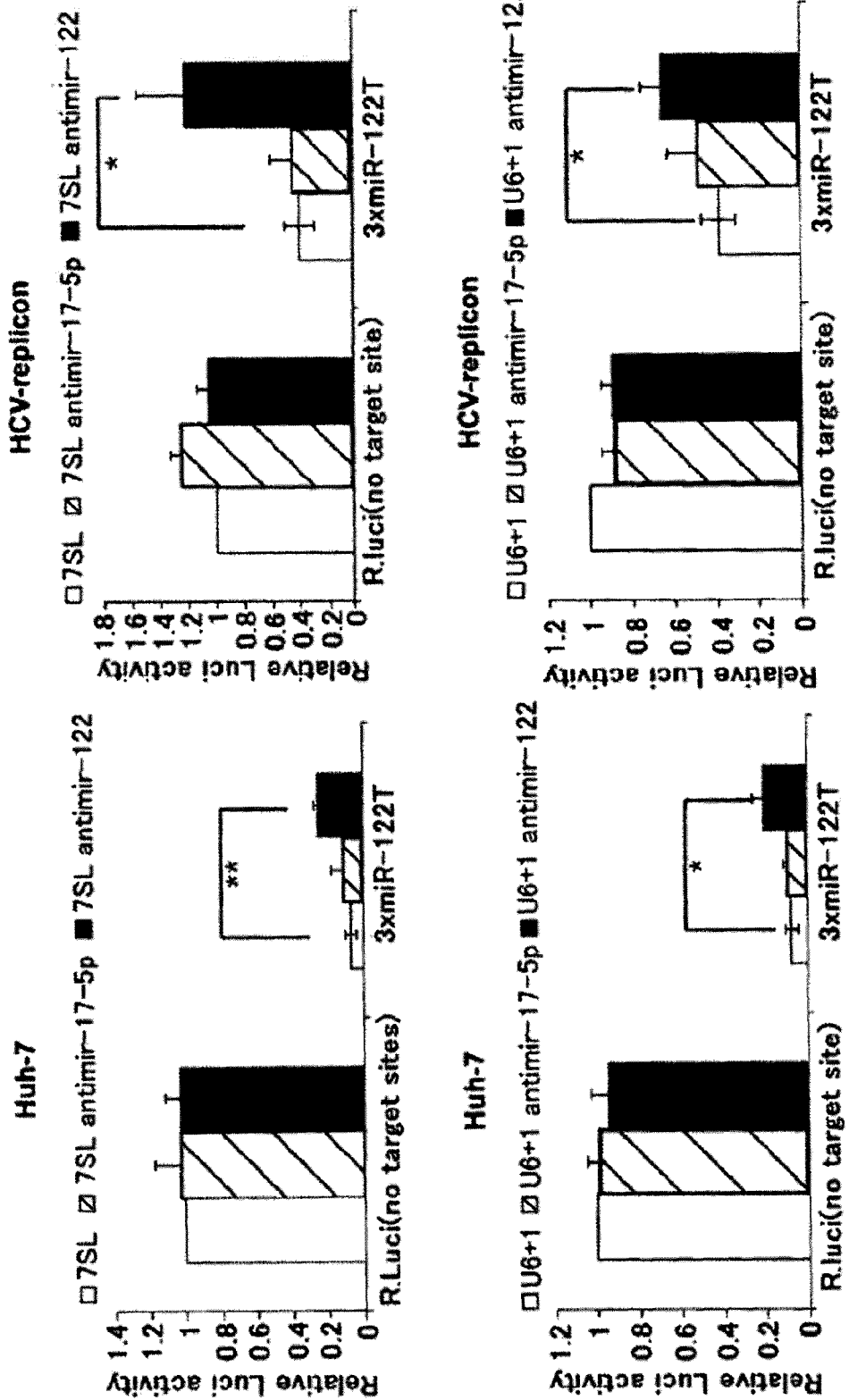
FIG. 6 demonstrates the expression of reporter gene induced by antimir-122.

FIG. 6 shows derepression of reporter gene activity by expression of antimir-122. Cells were cotransfected with miR-122T as control vector (con lane) alone or together with 7SL- or U6+1-based expression vector encoding anti-mature-miR-17-5p or anti-mature miR-122. The luciferase activity in the cotransfected cells were represented as relative to a control sample cotransfected with control vector with a reporter construct lacking miR-122 binding sites.

As shown in FIG. 6, intracellular expression of the anti-mature miR-122 resulted in derepression of reporter gene expression more highly in HCV replicon cells than in Huh-7 cells.

The above results suggest that intracellular expression of antisense sequence targeting the full sequence of mature miRNA was most effective with regard to miRNA silencing.

Example 3

Figure 7:
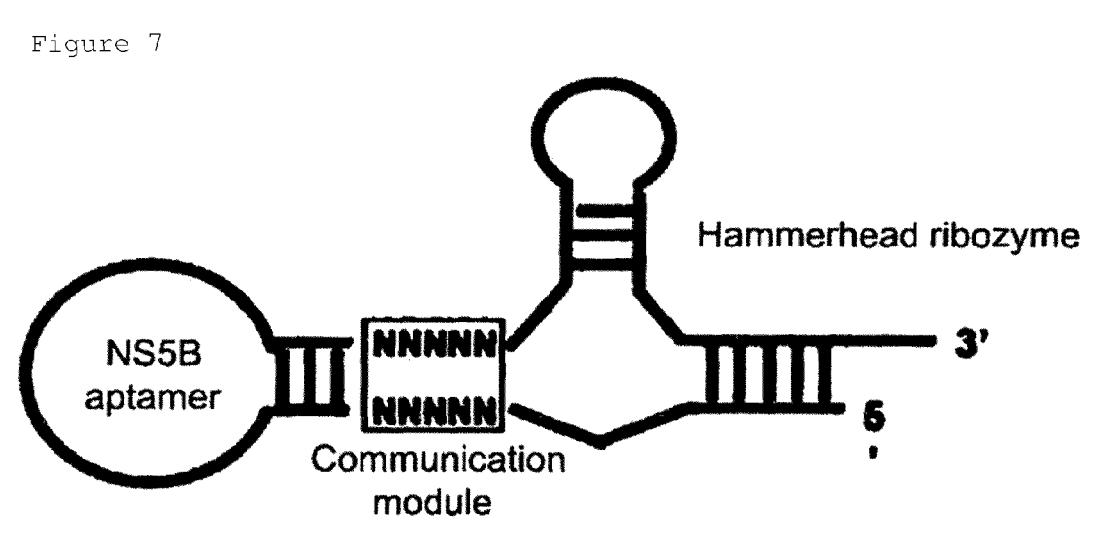

Selection of NS5B-Dependent Aptazyme 3-1. Generation of NS5B-Dependent Aptazyme Library To construct the NS5B-dependent aptazyme shown in FIG. 7, in vitro selection was performed using a ribozyme library consisting of aptamer against NS5B, ribozyme catalytic core region, and 10-mer randomized communication module sequence.

Ribozyme library RNA was generated by the in vitro transcription of DNA templates consecutively amplified two times with following primer sets that comprise 5 random sequences in the communication module, where N represents nucleotide with the equimolar incorporation of A, C, G, T at each position.

<First Primer Set>

```
                                              (SEQ ID No. 14)
5' primer:
5'-TTGGTGTCTGATGAGNNNNNCGCGCCATATTGTGAGGGGCGCG (SEQ ID No. 15)
3' primer:
5'-TACGTTTGGTTTCCCAAACGTTTCGNNNNNCGCGCCCCTCACAAT
```

<Second Primer Set>

```
                                              (SEQ ID No. 16)
5' primer:
5'-GGTAATACGACTCACTATAGGGTTGGTGTCTGATGAG (SEQ ID No. 17)
3' primer:
5'-TTTTTTTTTTTTTTTGGTGTTACGTTTGGTTTCCCAAA
```

3-2. Selection of NS5B-Dependent Aptazyme Library

To identify the most appropriate communication module sequence for inducing ribozyme activity dependent on the NS5B protein, RNA pool that could be nonspecifically self-cleaved was removed as follows.

After the ribozyme library was incubated at 37° C. for 6 hours in a ribozyme reaction buffer (20 mM Tris-HCl (pH 7.5), 300 mM NaCl, 4 mM DTT, 10 mM MgCl$_2$) with bovin serum albumin (BSA), uncleaved RNAs were isolated in a 7M urea-10% polyacrylamide gel and confirmed by EtBr dye.

Then, the undigested RNA pool was reverse-transcribed with oligodTprimer (5'-GGTAATACGACTCACTAT-AGGGTTGGTGTCTGATGAG, SEQ ID No. 16), and the resulting cDNAs were amplified with following primers.

```
                                              (SEQ ID No. 16)
5' primer:
5'-GGTAATACGACTCACTATAGGGTTGGTGTCTGATGAG (SEQ ID No. 17)
3' primer:
5'-TTTTTTTTTTTTTTTGGTGTTACGTTTGGTTTCCCAAA
```

The aptazyme pool was then synthesized by in vitro transcription of the cDNA and incubated with HCV NS5B protein at 37° C. for 1 hour in the ribozyme reaction buffer. Then NS5B-dependently cleaved aptazyme pool was purified in a polyacrylamide gel with urea. The purified aptazyme RNAs were amplified by reverse-transcription (primer: 5'-TTTTTTTTTTTTTTTGGTGT-TACGTTTGGTTTCCCAAA, SEQ ID No. 17) and PCR (5' primer; 5'-GGTAATACGACTCACTATAGGGTTGGT-GTCTGATGAG (SEQ ID No. 16), 3' primer: 5'-TTTTTTTTTTTTTTTGGTG TTACGTTTGGTTTC-CCAAA (SEQ ID No. 17)), and transcribed back to RNAs to prepare aptazyme RNA pool, which was then used for subsequent rounds of selection.

After 4 rounds of selection, the amplified DNA was cloned and the resulting 25 clones were sequenced. FIG. 8 shows 22 different clones that were selected with pyrimidine-rich communication module sequence.

3-3. Determination of NS5B-Dependent Aptazyme Specificity

To confirm the specificity of the selected NS5B-dependent aptazymes, the aptazymes were labeled with radioactive isotopes and incubated with BSA or HCV NS5B proteins.

First, labeling of the aptazyme RNAs was performed in a 20 μl reaction volume that contained 200 ng DNA template, [α-32 P] UTP (hot):cold UTP at a ratio of 1:4, 0.1 mM of ATP, CTP, and GTP, 10× transcription buffer, 10 mM DTT, 40 units of RNase inhibitor, and T7 RNA polymerase, and incubated for 3 hours at 37° C. Then the reaction mixture was added with 1.5 units of DNase I (promega) and incubated for additional 30 minutes at 37° C. to remove DNA template completely.

To determine the specificity of the selected aptazyme, 20 fmole aptazyme RNAs labeled with [α-32P] UTP were incubated with 3.2 pmole BSA and NS5B proteins. The 20 fmole aptazymes were denatured at 95° C. for 1 minute and 30 seconds, and refolded at 37° C. for 15 minutes. The aptazyme reaction mixture was then added with 2× hammerhead reaction buffer and 3.2 pmole protein and incubated at 37° C. for 1 hour. After completion of reaction, RNAs were mixed with RNA loading dye, denatured at 95° C., and separated on 7M-10% polyacrylamide gel at 180V for 1 hour. The separated RNAs on the gel were visualized by exposing it to X-ray film for 3 to 24 hours.

Figure 9:
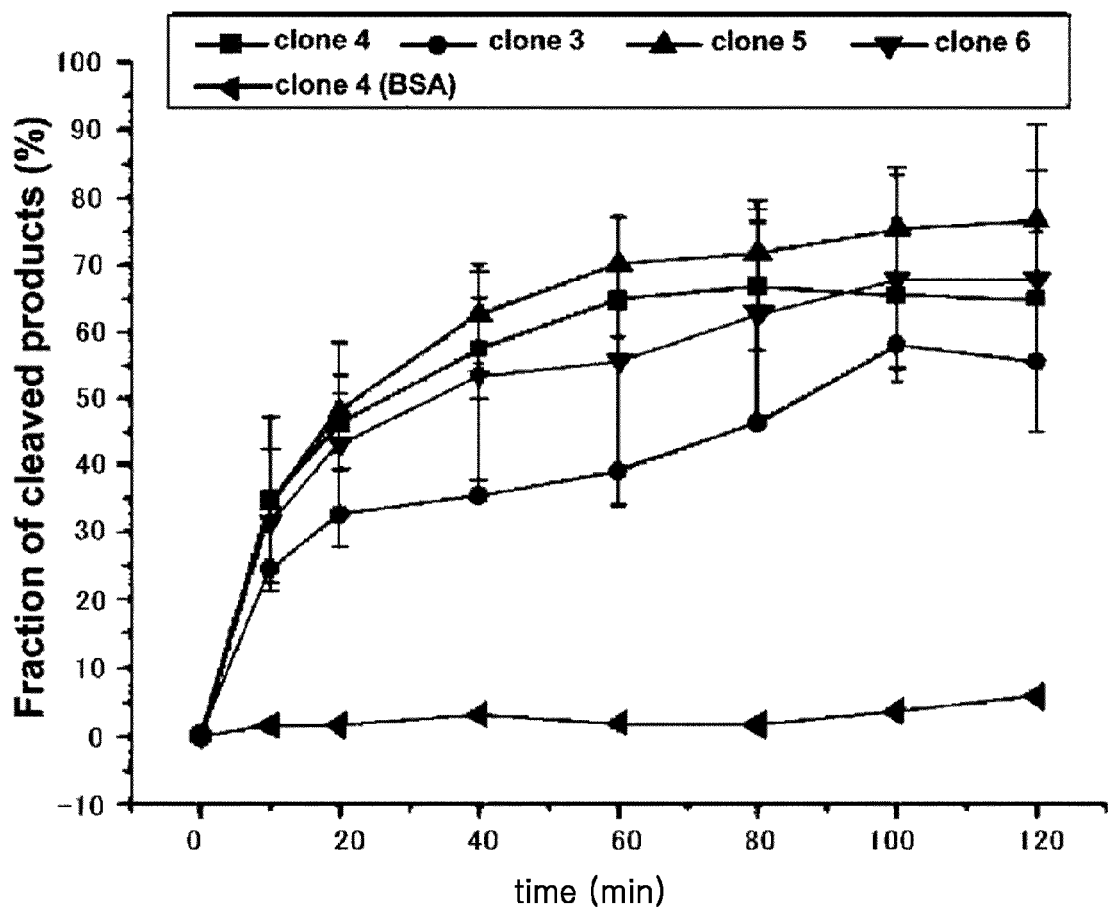
FIG. 9 is a graph showing quantitative analysis of the selected aptazyme reaction over time via phosphorimager.

FIG. 9 demonstrates the NS5B-selective self-cleavage activity of the NS5B-dependent aptazyme obtained in the present invention, suggesting that the NS5B-dependent aptazyme of the present invention can be self-cleaved only in the presence of NS5B protein.

Example 4

Evaluation of NS5B-Dependent Anti-miRNA Releasing Aptazyme Activity 4-1. Construction of NS5B-Dependent Anti-miRNA Releasing Aptazyme To construct NS5B-dependent antisense sequence to miR-17-5p or to miR-122 releasing allosteric ribozyme (referred to as antimir-17-5p NDAR and antimir-122 NDAR respectively); the released sequence from the selected ribozyme was replaced by the antisense sequence to mature miRNA 122 and miR-17-5p. For this, PCR was performed using selected allosteric ribozyme clone No. 4 cDNA as template with following primer sets.

<Antimir-17-5p NDAR>

```
                                              (SEQ ID No. 36)
5' primer: 5'-ACGCGTCGACGGGAGTGCAGCTGATGAG (SEQ ID No. 37)
3' primer: 5'-GCTCTAGACAAAGTGCTTACAGTGCAG
```

<Antimir-122 NDAR>

```
                                              (SEQ ID No. 18)
5' primer: 5'-ACGCGTCGACGGGAATGGTGCTGATGAG (SEQ ID No. 19)
3' primer: 5'-GCTCTAGATGGAGTGTGACAATGGTG
```

Each amplified DNA was digested with SalI and XbaI, and cloned into a pGEM T-easy vector (Promega). Each NDAR was generated by in vitro transcription using the cloned vector as the template. To construct the expression vector for each NDAR in cells, each vector containing NDAR cDNA was digested with SalI and XbaI and cloned into the U6+1 snRNA promoter-driven expression cassettes.

FIG. 10 shows the nucleotide sequence and expected secondary structure of antimir-122 NDAR and antimir-17-5p NDAR.

4-2. In Vitro Self-Cleavage Assay of NDAR

The in vitro transcribed NDAR RNA was dephosphorylated with calf intestine alkaline phosphatase (Ambion) and 5'-end-labeled with [γ-32P] ATP (3000 Ci/mmol, Amersham) and T4 polynucleotide kinase (Ambion). The end-labeled NDAR RNA (20 fmol) was incubated with 3.2 pmol of BSA or HCV NS5B at 37° C. for 1 hour in a reaction buffer (30 mM Tris-HCl (pH 7.5), 150 mM NaCl, 5 mM $MgCl_2$, 2 mM dithiothreitol), and the reacted products were separated on a 12% polyacrylamide gel with 7M urea.

To identify self-cleavage sites by the ribozymes, a sequence ladder was generated and loaded on the gel as a size marker as follows. Alkaline hydrolysis was performed at 95° C. for 15 minutes in a 20 µl reaction volume that contained 50 mM $NaHCO_3$ (pH 9.0), 1 mM EDTA, 0.25 mg/mL tRNA, and 54 fmole of NDAR RNA. The cleaved NDAR RNA fragments were denatured at 80° C. for 5 minutes and analyzed on the denaturing polyacrylamide gel.

NDAR RNA (54 fmol) was also digested with RNase T1 (USB) at 37° C. for 10 minutes in a 20 µl reaction mixture containing 20 mM sodium citrate (pH 5.0), 7M urea, 1 mM EDTA, 0.25 mg/mL tRNA, and 1 unit of RNase T1. The nuclease-treated reactions were stopped by the addition of 10 µl of RNA loading dye (10 ml formamide, 10 mMEDTA, 0.01% bromophenol blue, 0.01% xylene cyanol) and analyzed on the denaturing polyacrylamide gel.

To confirm the exact self-cleavage sites by the ribozymes, 3'-rapid amplification of cDNA ends (RACE) PCR of the cleaved products was performed as follows. First, self-cleaved RNA (30 pmol) was isolated from the polyacrylamide gel with urea and extended with poly(A)-tail using poly (A) polymerase (5 units, NEB) at 37° C. for 30 minutes. Poly (A) RNA was reverse transcribed with 3'-RACE primer 5'-AAGCAGTGGTATCAACGCAGAGTAC(T)30VN (SEQ ID No. 38), where N represents nucleotide equimolar incorporation of A, T, G, C while V denotes A, G, or C.

The resulting cDNA was then amplified by PCR with a 5'primer specific for the 5' end of the ribozyme (primer for antimir-122 NDAR: 5'-TAATACGACTCACTATAGG-GAATGGTGCTG (SEQ ID No. 39); primer for antimir-17-5p NDAR: 5'-TAATACGACTCACTATAGGGAGTG-CAGCTG (SEQ ID No. 40)) and nested 3' primer (5'-AAGCAGTGGTATCAACGCAGAGT, SEQ ID No. 41) at 98° C. for 30 seconds, at 58° C. for 30 seconds, at 72° C. for 30 seconds for 25 cycles.

FIG. 10 shows the nucleotide sequence and expected secondary structure of antimir-122 NDAR and antimir-17-5p NDAR and the self-cleavage sites identified by the sequencing gel analysis after in vitro self-cleavage assay and the 3'-RACE method. As shown in FIG. 10, antimir-122 NDAR and antimir-17-5p NDAR were self-cleaved only in the presence of HCV NS5B.

The analysis of the cleaved RNA products on the sequencing gel confirms that the self-cleavage occurred near the expected cleavage site of NDAR. This result suggests that the antisense sequence targeting miRNA is released by antimir NDAR.

4-3. Anti-miRNA Reporter Assay

To determine whether the antimir-122 NDAR expression vector inhibits microRNA-122 activity selectively in the HCV-replicating cells, the following experiment was performed.

First, 25 ng pCMV-F. luci and 100 ng of pTKRL-3× miR122T or reporter construct lacking miR-122 binding sites [R. Luci (no target site)] were cotransfected with 400 ng of 7SL- or U6+1-based anti-miRNA expression vector into 1×10^5 Huh-7 and HCV replicon Huh-7 cells using LT1 transfection agent (Mirus). After 24 hours of transfection, the cells were harvested and lysed, and reporter gene expression activities were determined by measuring relative light units using a TD-20/20 luminometer (Turner Designs Instrument) and dual-luciferase reporter assay system (Promega). For analysis of selective anti-miRNA activity by allosteric ribozyme expression vectors, after 48 hours of cotransfection of pCMV-F.luci (25 ng) and pTK-RL-3×miR122T (200 ng) with antimir NDAR expression vector (400 ng), reporter activities were assessed.

FIG. 11 shows selective inhibition of miRNA-122 activity by antimir-122 NDAR in HCV replicon cells. Cells were cotransfected with 3×miR122T and control 7SL vector, or with 7SL-driven expression vector for antimir-122, antimir-122 NADR or antimir-122 NDAR4. The transfection of reporter construct without any miRNA target sequence was used as a control.

As shown in FIG. 11, the expression of antisense sequence to mature miR-122 inhibited miRNA activity and as a result, reporter activity was induced in Huh-7 cells regardless of HCV replication. In contrast, the expression of antimir-122NDAR induced high activation of reporter gene in HCV-replicon Huh cells, which was not observed in Huh cells. These results suggest that the expression of antimir-122 NDAR can selectively and efficiently increase the expression of reporter gene in HCV replicon cells.

Example 5

Immunoblot Assay

HCV-dependent inhibition of miR-122 activity by antimir-122 NDAR was confirmed by western blotting of intrinsic miR-122 targeting protein Cyclin G1(CCNG1)(Gramantieri L, Ferracin M, Fornari F, Veronese A, Sabbioni S, Liu C G, et al. Cyclin G1 is a target of miR-122a, a microRNA frequently down-regulated in human hepatocellular carcinoma. Cancer Res 2007; 67:6092-6099) and adolaseA (AldoA)(Elmen J, Lindow M, Silahtaroglu A, Bak M, Christensen M, Lind-Thomsen A, et al. Antagonism of microRNA-122 in mice by systemically administered LNA-antimiR leads to up-regulation of a large set of predicted target mRNAs in the liver. Nucleic Acids Res 2008; 36:1153-1162).

HCV replicon cells in 60 mm dishes (each containing 8×10^5 cells) were transfected with 7SL-driven NDAR construct (1 µg) using TransIT LT1 transfection reagent (Mirus Bio, Madison) according to the manufacturer's protocol. Cells were lysed 30 hours after transfection in a buffer consisting of 50 mM Tris/HCl (pH 8.0), 150 mM NaCl, 0.2% sodium azide, 0.1% SDS, 0.1% NP-40, and 0.5% sodium deoxycholate. The total proteins (50 µg) in the cell lysates were loaded into SDS-polyacrylamide gel and transferred on PVDF membrane (Bio-Rad) using electrophoresis in a condition of 300 mA for 3 hours at 4° C. The membrane was blocked with 5% (v/v) skim milk and immunoblotting was performed using the following primary antibodies: mouse monoclonal anti-NS5A (#MAB8694; Millipore, Billerica), goat polyclonal anti-Aldolase A (#sc-12059; Santa Cruz Biotechnology), rabbit polyclonal anti-Cyclin G1 (#C-18; Santa Cruz Biotechnology), and mouse anti-u-Tubulin (#DM1a; Santa Cruz Biotechnology). The following secondary antibodies were used: goat anti-mouse IgG-HRP (#sc-2005; Santa Cruz Biotechnology), mouse anti-goat IgG-HRP (#sc-23521; Santa Cruz Biotechnology), and goat anti-rabbit IgG-HRP (#sc-2004; Santa Cruz Biotechnology). The protein bands were visualized by an enhanced chemiluminescence protocol (Amersham-Pharmacia Biotech).

Figure 12:
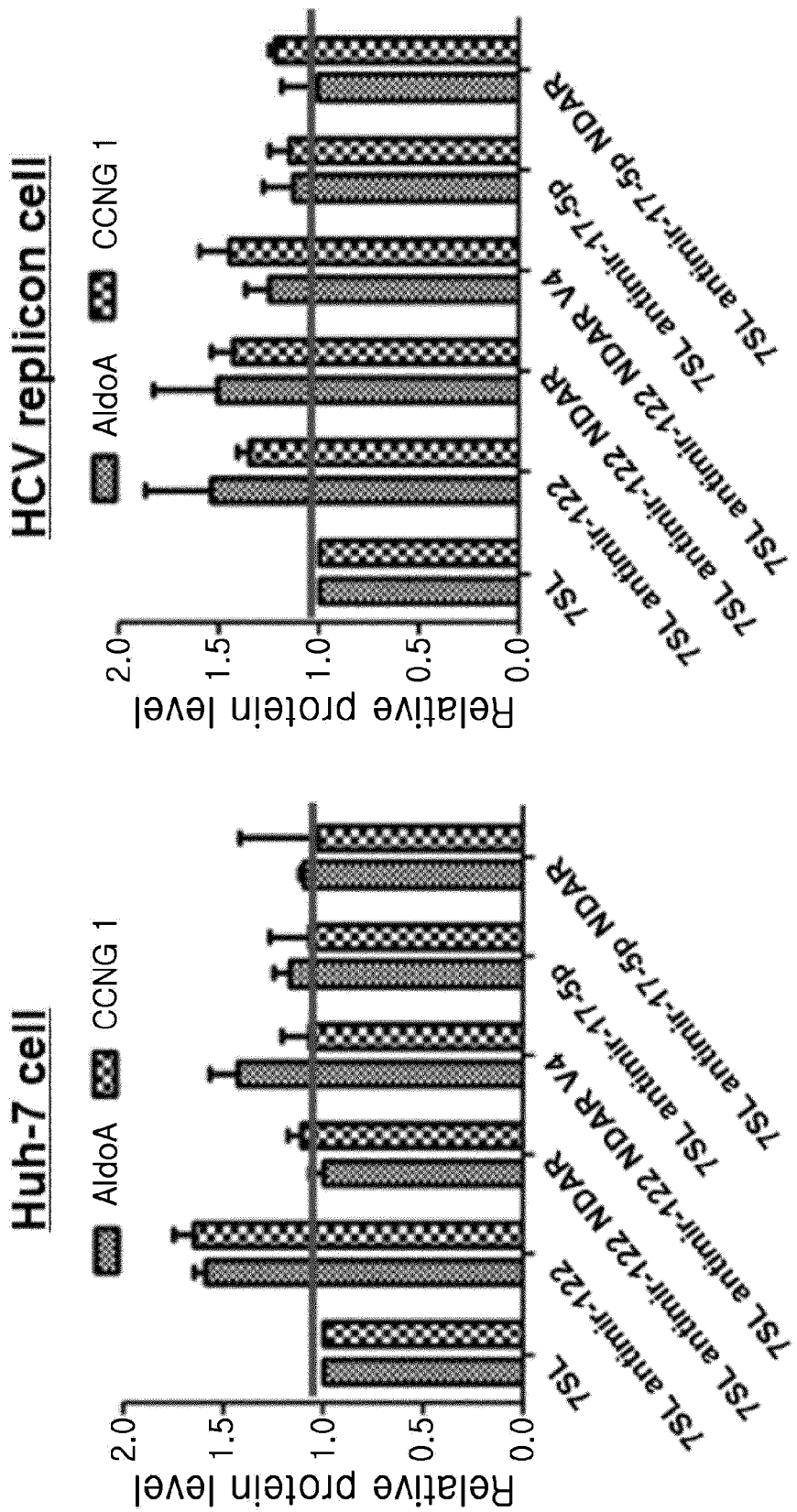
FIG. 12 demonstrates Selective deregulation of cellular targets of miR-122 by antimir-122 NDAR in HCV replicon cells.

FIG. 12 shows the selective deregulation of cellular targets of miR-122 by antimir-122 NDAR in HCV replicon cells. The expression of antimir-122 induced the expression of two miR-122 target proteins regardless of HCV replication. As similar to the results shown in FIG. 11, the expression of antimir-122 NDAR increased the expression of cellular miR-122 target proteins selectively in HCV replicon Huh-7 cells. However, the expression of miR-122 target protein was not affected by the expression of antimir-17-5p or antimir-17-5p-NDAR, which demonstrates the specificity of corresponding antimir towards target miRNA.

The above results suggest that the intracellular expression of the mature miRNA-targeting antimir-122 releasing allosteric ribozyme specifically activates ribozyme activity and hence releases an antisense sequence against the miRNA in the presence of HCV NS5B, resulting in the efficient and specific inhibition of miR-122 activity only in HCV-replicating cells.

Example 6

MiRNA-Specific Quantitative RT-PCR

HCV replicon cells in a 12-well plate (each well containing 2×10^5 cells) were transfected with 7SL-driven NDAR construct (1 µg) using TransIT LT1 transfection reagent (Mirus Bio) according to the manufacturer's protocol. At 30 hours after transfection, total RNA was isolated and reverse transcribed with 3' primer specific for the negative strand of HCV cDNA (5'CGTAACACCAACGGGCGCGCCATG, SEQ ID No. 42) or random primer for 18S cDNA. The resultant cDNA were subsequently amplified with 2× real-time PCR (RT-PCR) premix (Solgent Co.) with forward (5'CGTAACACCAACGGGCGCGCCATG, SEQ ID No. 42) and reverse primer (5'CTCGTCCTGCAGTTCATTCAGGGC, SEQ ID No. 43) specific for the neomycin resistant marker gene of the HCV replicon construct. RT-PCR was performed using the Rotor-Gene (Corbett) and SYBR Green PCR Core Reagents (PE Biosystems), according to the manufacturer's protocol. The conditions for the PCRs were 95° C. for 30 seconds, 58° C. for 30 seconds, and 72° C. for 30 seconds for 40 cycles. The threshold levels obtained from the HCV were adjusted to the threshold levels found in the 18S PCR reaction (forward primer; 5'GTAACCCGTTGAACCCCATT (SEQ ID No. 44), reverse primer; 5'CCATCCAATCGGTAGTAGCG (SEQ ID No. 45)) to correct for minor variation in cDNA loading. Quantification of miR-17-5p and miR-122 was performed using TaqMan MicroRNA kit (miR-17-5p: 002308, miR-122: 002245; Applied Biosystem) according to the manufacturer's instructions. The 18S RNA was used as an internal control.

Figure 13:
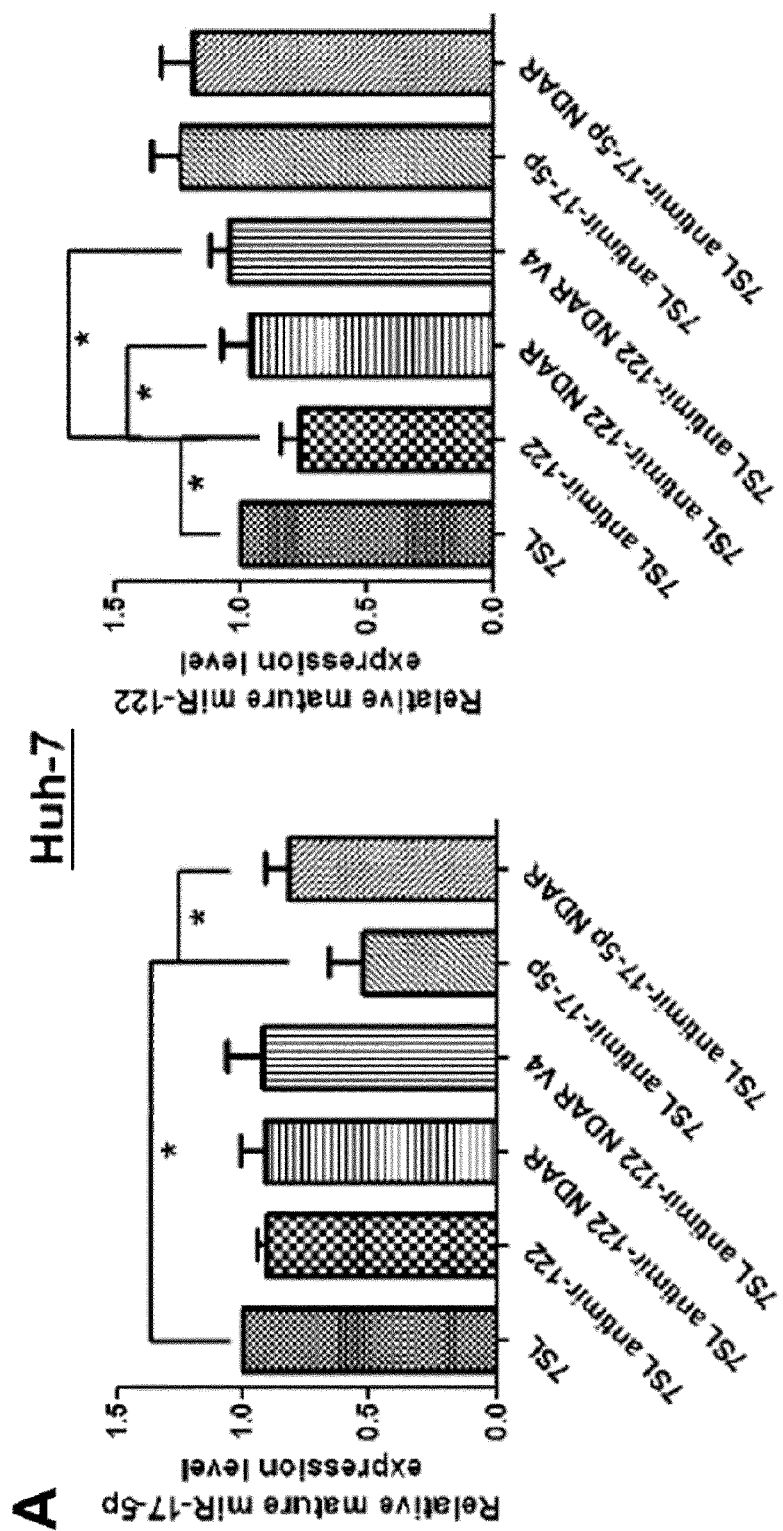
FIG. 13 shows HCV-specific inhibition of miRNA amplification by antimir NDAR. Huh-7 (A) or HCV replicon cells (B).
Figure 13:
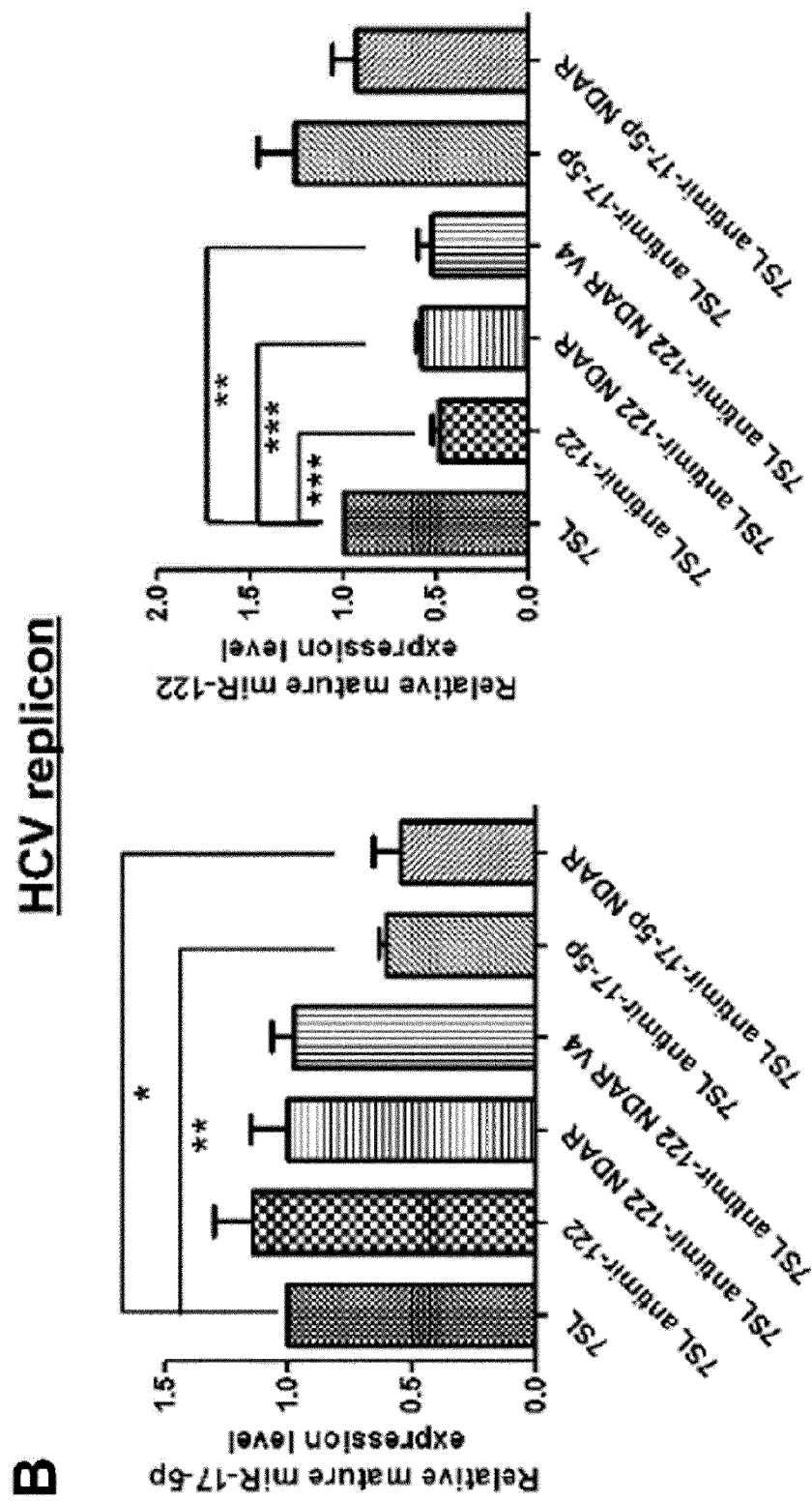

FIG. 13 demonstrates that the expression of antimir NDAR selectively inhibits the amplification of target miRNA only in HCV replicon cells.

Example 7

Anti-HCV Activity of NDAR

In this experiment, anti-HCV activity of the NDAR in human cells stably supporting HCV subgenomic replicon replication was evaluated. To this end, the level of HCV negative (−) strand RNA and HCV NS5A protein was quantified in the HCV replicon cells transfected with the expression vector encoding antimir-122 NDAR.

Figure 14:
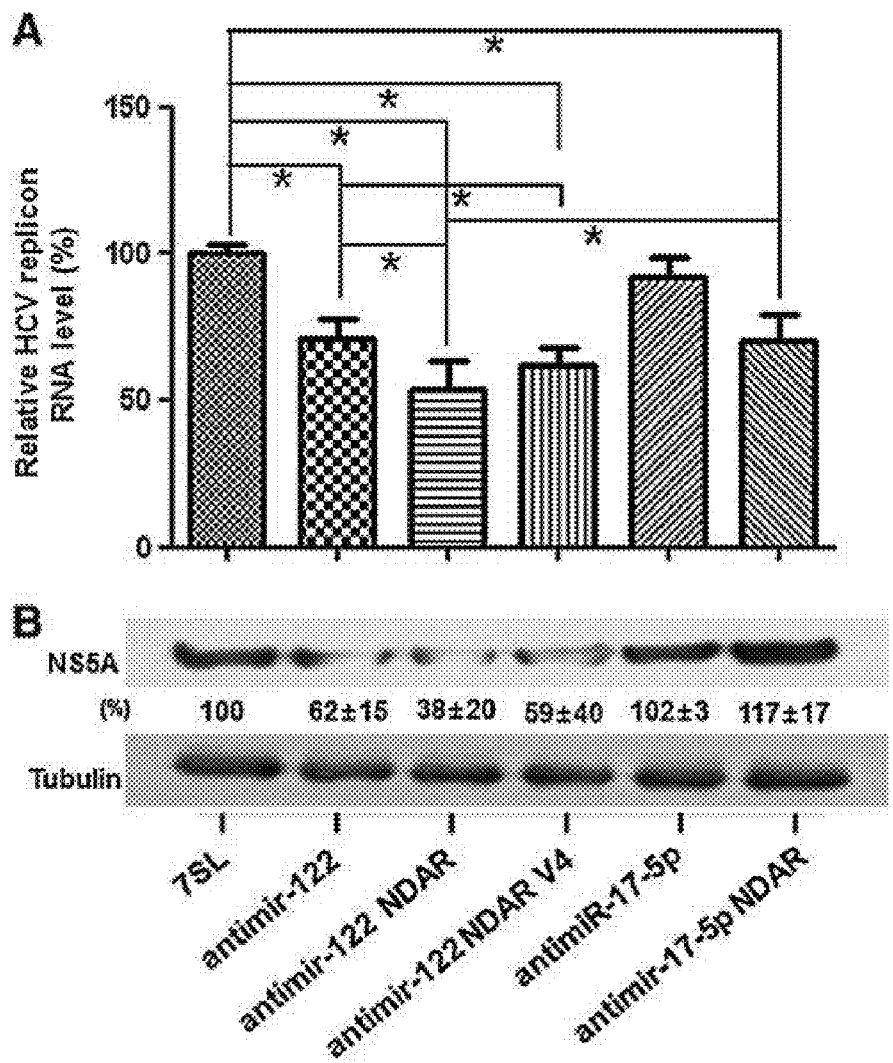
FIG. 14 demonstrates inhibition of HCV replicon replication by antimir-122 NDAR.

FIG. 14(A) shows the analysis of the HCV(−) subgenomic RNA level using real-time PCR and 14(B) shows the quantification of HCV NS5A protein using western blot analysis. Expression of antimir-122 inhibited HCV replication by up to 26%. In contrast, HCV replication was not affected by unrelated antimir-17-5p, indicating specific up-regulation of HCV replication by miR-122. Expression of antimir-17-5p NDAR also inhibited HCV replication by up to 30%. This inhibition was probably due to sequestration of HCV NS5B protein by aptamer. Noticeably, expression of antimir-122 NDAR suppressed HCV replication the most, by up to 47%, indicating that the intracellular expression of the allosteric ribozyme deactivates miR-122 activity simultaneously with inhibiting HCV NS5B function and hence induces synergistic effects on the HCV replication.

Figure 15:
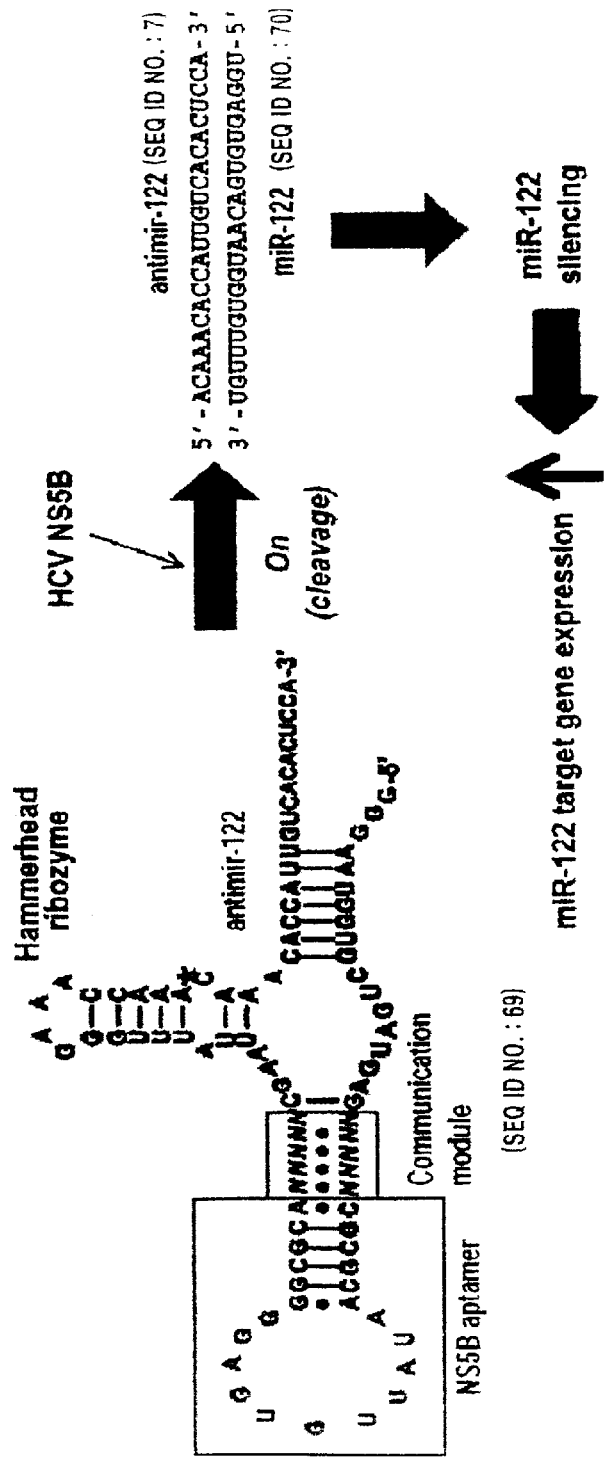
FIG. 15 is a schematic diagram showing the process of inhibiting microRNA-122 activity by NS5B-dependent antimir-122 NDAR through releasing antisense sequence to microRNA-122.

These results suggest that the self-cleavage activity of the present aptazyme is specifically activated to release antisense sequence against mature miRNA only in the presence of HCV NS5B, thereby inhibiting miR-122 activity efficiently and selectively in the HCV-infected cells (refer to FIG. 15). Furthermore, the aptazyme of the present invention inhibits HCV NS5B protein function by specifically binding to HCV NS5B protein through its aptamer, thereby inhibiting HCV proliferation selectively in HCV-infected cells.

What is claimed is:

1. An aptazyme capable of releasing an antisense sequence to microRNA specifically in HCV-infected cells, comprising:

an aptamer for hepatitis C virus (HCV) RNA-encoding component;

a hammerhead ribozyme comprising an antisense sequence to microRNA at the site released by self-cleavage; and a communication module sequence that connects the aptamer and hammerhead ribozyme and includes self-cleavage activity of hammerhead ribozyme upon binding of the aptamer with the HCV RNA-encoding component, wherein nucleic acid sequence of the aptazyme is represented by SEQ ID NO: 12 or 13.

2. A composition for treatment of a HCV-related disease, comprising the aptazyme according to claim 1.

3. The composition according to claim 2, wherein the HCV-related disease is selected from the group consisting of hepatitis, liver fibrosis, liver cirrhosis, and liver cancer.

4. A method for treatment of HCV-related diseases comprising the step of administering the composition comprising the aptazyme of claim 1 to HCV carriers or subjects with HCV-related disease.

* * * * *